(12) United States Patent
Yadin

(10) Patent No.: US 9,427,340 B2
(45) Date of Patent: Aug. 30, 2016

(54) STENT WITH PROTRUDING BRANCH PORTION FOR BIFURCATED VESSELS

(75) Inventor: Amnon Yadin, Kfar Vitkin (IL)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 3014 days.

(21) Appl. No.: 11/706,082

(22) Filed: Feb. 14, 2007

(65) Prior Publication Data

US 2007/0142902 A1  Jun. 21, 2007

Related U.S. Application Data

(63) Continuation-in-part of application No. 11/010,730, filed on Dec. 14, 2004.

(51) Int. Cl.
*A61F 2/90* (2013.01)
*A61F 2/856* (2013.01)
*A61F 2/91* (2013.01)
*A61F 2/915* (2013.01)

(52) U.S. Cl.
CPC .............. *A61F 2/856* (2013.01); *A61F 2/91* (2013.01); *A61F 2/915* (2013.01); *A61F 2002/91508* (2013.01); *A61F 2002/91516* (2013.01); *A61F 2002/91525* (2013.01); *A61F 2002/91533* (2013.01); *A61F 2002/91558* (2013.01)

(58) Field of Classification Search
CPC ........................................................ A61F 2/90
USPC ........................................................ 623/1.35
See application file for complete search history.

(56) References Cited

U.S. PATENT DOCUMENTS

| 4,309,994 A | 1/1982 | Grunwald ................. 128/214 R |
| 4,769,005 A | 9/1988 | Ginsburg et al. ............... 604/53 |
| 4,774,949 A | 10/1988 | Fogarty ..................... 128/348.1 |
| 4,896,670 A | 1/1990 | Crittenden .................... 606/194 |
| 4,905,667 A | 3/1990 | Foerster et al. .................. 128/4 |

(Continued)

FOREIGN PATENT DOCUMENTS

| CA | 2220864 | 7/1999 |
| DE | 9014845 | 2/1991 |

(Continued)

OTHER PUBLICATIONS

U.S. Appl. No. 11/010,730, filed Dec. 14, 2004, Yadin et al.

(Continued)

*Primary Examiner* — Matthew Schall
(74) *Attorney, Agent, or Firm* — Seager, Tufte & Wickhem, LLP

(57) ABSTRACT

In at least one embodiment, a stent comprises a plurality of interconnected framework members defining a plurality of cells. A side branch structure comprises a first serpentine ring extending around an inner side branch cell, a second serpentine ring extending around the first serpentine ring and a plurality of side branch connectors. The first serpentine ring comprises a plurality of curved portions including convex curved portions and concave curved portions. The convex curved portions include first convex curved portions and second convex curved portions, wherein the second convex curved portions are located farther away from a side branch center point than the first convex curved portions. Each side branch connector extends between a concave curved portion of the first serpentine ring and a portion of the second serpentine ring.

20 Claims, 21 Drawing Sheets

(56) References Cited

U.S. PATENT DOCUMENTS

| | | | |
|---|---|---|---|
| 4,994,071 A | 2/1991 | MacGregor | 606/194 |
| 5,342,387 A | 8/1994 | Summers | 606/198 |
| 5,387,235 A | 2/1995 | Chuter | 623/1 |
| 5,456,712 A | 10/1995 | Maginot | 623/1 |
| 5,476,471 A | 12/1995 | Shifrin et al. | 606/151 |
| 5,591,228 A | 1/1997 | Edoga | 623/1 |
| 5,607,444 A | 3/1997 | Lam | 606/194 |
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |
| 5,632,772 A | 5/1997 | Alcime et al. | 623/1 |
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |
| 5,697,971 A | 12/1997 | Fischell et al. | 623/1 |
| 5,709,713 A | 1/1998 | Evans et al. | 623/1 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,755,773 A | 5/1998 | Evans et al. | 623/1 |
| 5,755,778 A | 5/1998 | Kleshinski | 623/1 |
| 5,782,906 A | 7/1998 | Marshall et al. | 623/1 |
| 5,824,036 A | 10/1998 | Lauterjung | 623/1 |
| 5,824,040 A | 10/1998 | Cox et al. | 623/1 |
| 5,827,320 A | 10/1998 | Richter et al. | 606/194 |
| 5,851,464 A | 12/1998 | Davila et al. | 264/103 |
| 5,868,777 A | 2/1999 | Lam | 606/194 |
| 5,893,887 A | 4/1999 | Jayaraman | 623/1 |
| 5,906,640 A | 5/1999 | Penn et al. | 623/1 |
| 5,922,021 A | 7/1999 | Jang | 623/1 |
| 5,961,548 A | 10/1999 | Shmulewitz | 623/1 |
| 5,972,017 A | 10/1999 | Berg et al. | 606/198 |
| 6,013,054 A | 1/2000 | Jiun Yan | 604/96 |
| 6,013,091 A | 1/2000 | Ley et al. | 606/191 |
| 6,017,324 A | 1/2000 | Tu et al. | 604/96 |
| 6,017,363 A | 1/2000 | Hojeibane | 623/1 |
| 6,030,414 A | 2/2000 | Taheri | 623/1 |
| 6,033,434 A | 3/2000 | Borghi | 623/1 |
| 6,033,435 A | 3/2000 | Penn et al. | 623/1 |
| 6,048,361 A | 4/2000 | Von Oepen | 623/1 |
| 6,056,775 A | 5/2000 | Borghi et al. | 623/1.16 |
| 6,059,824 A | 5/2000 | Taheri | 623/1 |
| 6,068,655 A | 5/2000 | Seguin et al. | 623/1 |
| 6,086,611 A | 7/2000 | Duffy et al. | 623/1 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,123,721 A | 9/2000 | Jang | 623/1 |
| 6,129,738 A | 10/2000 | Lashinski et al. | 606/194 |
| 6,129,754 A | 10/2000 | Kanesaka et al. | 623/1 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,183,509 B1 | 2/2001 | Dibie | 623/1.35 |
| 6,203,568 B1 | 3/2001 | Lombardi et al. | 623/1.13 |
| 6,210,380 B1 | 4/2001 | Mauch | 604/284 |
| 6,210,429 B1 | 4/2001 | Vardi et al. | 623/1.11 |
| 6,210,433 B1 | 4/2001 | Larre | 623/1.15 |
| 6,254,593 B1 | 7/2001 | Wilson | 606/1.11 |
| 6,258,115 B1 | 7/2001 | Dubrul | 606/200 |
| 6,258,116 B1 * | 7/2001 | Hojeibane | 623/1.16 |
| 6,261,305 B1 | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,290,673 B1 | 9/2001 | Shanley | 604/102.02 |
| 6,325,822 B1 | 12/2001 | Chouinard et al. | 623/1.35 |
| 6,325,826 B1 | 12/2001 | Vardi et al. | 623/1.35 |
| 6,334,864 B1 | 1/2002 | Amplatz et al. | 606/200 |
| 6,334,870 B1 | 1/2002 | Ehr et al. | 623/1.16 |
| 6,346,089 B1 | 2/2002 | Dibie | 603/1.15 |
| 6,348,065 B1 | 2/2002 | Brown et al. | 623/1.16 |
| 6,355,060 B1 | 3/2002 | Lenker et al. | 623/1.34 |
| 6,361,544 B1 | 3/2002 | Wilson et al. | 606/194 |
| 6,361,555 B1 | 3/2002 | Wilson | 623/1.11 |
| 6,383,213 B2 | 5/2002 | Wilson et al. | 623/1.11 |
| 6,395,018 B1 | 5/2002 | Castaneda | 623/1.13 |
| 6,436,104 B2 | 8/2002 | Hojeibane | 606/108 |
| 6,436,134 B2 | 8/2002 | Richter et al. | 623/1.15 |
| 6,478,816 B1 | 11/2002 | Kveen et al. | 623/1.15 |
| 6,508,836 B2 | 1/2003 | Wilson et al. | 623/1.35 |
| 6,517,558 B2 | 2/2003 | Gittings et al. | 606/153 |
| 6,520,988 B1 | 2/2003 | Colombo et al. | 623/1.35 |
| 6,540,779 B2 | 4/2003 | Richter et al. | 623/1.35 |
| 6,579,309 B1 | 6/2003 | Loos et al. | 623/1.16 |
| 6,579,312 B2 | 6/2003 | Wilson et al. | 623/1.35 |
| 6,582,394 B1 | 6/2003 | Reiss et al. | 604/96.01 |
| 6,596,020 B2 | 7/2003 | Vardi et al. | 623/1.11 |
| 6,599,316 B2 | 7/2003 | Vardi et al. | 623/1.15 |
| 6,645,242 B1 | 11/2003 | Quinn | 623/1.16 |
| 6,689,156 B1 | 2/2004 | Davidson et al. | 623/1.11 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,749,628 B1 | 6/2004 | Cho et al. | 623/1.15 |
| 6,776,793 B2 | 8/2004 | Brown et al. | 623/1.15 |
| 6,811,566 B1 | 11/2004 | Penn et al. | 623/1.15 |
| 6,835,203 B1 * | 12/2004 | Vardi et al. | 623/1.34 |
| 6,858,038 B2 | 2/2005 | Heuser | 623/1.35 |
| 6,884,258 B2 | 4/2005 | Vardi et al. | 623/1.11 |
| 6,896,699 B2 | 5/2005 | Wilson et al. | 623/1.35 |
| 6,932,837 B2 | 8/2005 | Amplatz et al. | 623/1.15 |
| 6,955,687 B2 | 10/2005 | Richter et al. | 623/1.35 |
| 6,955,688 B2 | 10/2005 | Wilson et al. | 623/1.35 |
| 6,962,602 B2 | 11/2005 | Vardi et al. | 623/1.11 |
| 7,018,400 B2 | 3/2006 | Lashinski et al. | 623/1.11 |
| 7,060,091 B2 | 6/2006 | Killion et al. | 623/1.15 |
| 7,220,275 B2 * | 5/2007 | Davidson et al. | 623/1.35 |
| 7,341,598 B2 * | 3/2008 | Davidson et al. | 623/1.35 |
| 7,537,609 B2 * | 5/2009 | Davidson et al. | 623/1.35 |
| 7,578,841 B2 * | 8/2009 | Yadin et al. | 623/1.35 |
| 7,678,142 B2 * | 3/2010 | Vardi et al. | 623/1.35 |
| 2001/0003161 A1 | 6/2001 | Vardi et al. | 623/1.11 |
| 2001/0004706 A1 | 6/2001 | Hojeibane | 623/1.11 |
| 2001/0004707 A1 | 6/2001 | Dereurne et al. | 623/1.16 |
| 2001/0012927 A1 | 8/2001 | Mauch | 604/284 |
| 2001/0016766 A1 | 8/2001 | Vardi et al. | 623/1.11 |
| 2001/0016767 A1 | 8/2001 | Wilson et al. | 623/1.11 |
| 2001/0016768 A1 | 8/2001 | Wilson et al. | 623/1.11 |
| 2001/0025195 A1 | 9/2001 | Shaolian et al. | 623/1.13 |
| 2001/0027291 A1 | 10/2001 | Shanley | 604/104 |
| 2001/0027338 A1 | 10/2001 | Greenberg | 623/1.13 |
| 2001/0029396 A1 | 10/2001 | Wilson et al. | 623/1.11 |
| 2001/0037116 A1 | 11/2001 | Wilson et al. | 606/108 |
| 2001/0037138 A1 | 11/2001 | Wilson et al. | 623/1.11 |
| 2001/0039448 A1 | 11/2001 | Dibie | 623/1.16 |
| 2001/0049552 A1 | 12/2001 | Richter et al. | 623/1.15 |
| 2001/0056297 A1 | 12/2001 | Hojeibane | 623/1.16 |
| 2002/0013618 A1 | 1/2002 | Marotta et al. | 623/1.15 |
| 2002/0013619 A1 | 1/2002 | Shanley | 623/1.15 |
| 2002/0022874 A1 | 2/2002 | Wilson | 623/1.11 |
| 2002/0026232 A1 | 2/2002 | Marotta et al. | 623/1.16 |
| 2002/0035392 A1 | 3/2002 | Wilson | 623/1.11 |
| 2002/0042650 A1 | 4/2002 | Vardi et al. | 623/1.35 |
| 2002/0052648 A1 | 5/2002 | McGuckin, Jr. et al. | 623/1.15 |
| 2002/0072790 A1 | 6/2002 | McGuckin, Jr. et al. | 623/1.12 |
| 2002/0095208 A1 | 7/2002 | Gregorich et al. | 623/1.15 |
| 2002/0111675 A1 | 8/2002 | Wilson | 623/1.35 |
| 2002/0156516 A1 | 10/2002 | Vardi et al. | 623/1.11 |
| 2002/0156517 A1 | 10/2002 | Perouse | 623/1.11 |
| 2002/0165604 A1 | 11/2002 | Shanley | 623/1.15 |
| 2002/0173835 A1 | 11/2002 | Bourang et al. | 623/1.11 |

(56) References Cited

U.S. PATENT DOCUMENTS

| | | | |
|---|---|---|---|
| 2002/0173840 A1 | 11/2002 | Brucker et al. | 623/1.16 |
| 2002/0183763 A1 | 12/2002 | Callol et al. | 606/108 |
| 2002/0193872 A1 | 12/2002 | Trout, III et al. | 623/1.34 |
| 2002/0193873 A1 | 12/2002 | Brucker et al. | 623/1.35 |
| 2003/0009209 A1 | 1/2003 | Hojeibane | 623/1.11 |
| 2003/0028233 A1 | 2/2003 | Vardi et al. | 623/1.11 |
| 2003/0050688 A1 | 3/2003 | Fischell et al. | 623/1.15 |
| 2003/0055483 A1 | 3/2003 | Gumm | 623/1.11 |
| 2003/0074047 A1 | 4/2003 | Richter | 623/1.11 |
| 2003/0093109 A1 | 5/2003 | Mauch | 606/194 |
| 2003/0097169 A1 | 5/2003 | Brucker | 623/1.11 |
| 2003/0114912 A1 | 6/2003 | Sequin et al. | 623/1.11 |
| 2003/0125791 A1 | 7/2003 | Sequin et al. | 623/1.11 |
| 2003/0125802 A1 | 7/2003 | Callol et al. | 623/1.35 |
| 2003/0135259 A1 | 7/2003 | Simso | 623/1.12 |
| 2003/0181923 A1 | 9/2003 | Vardi | 606/108 |
| 2003/0195606 A1* | 10/2003 | Davidson et al. | 623/1.11 |
| 2004/0006381 A1 | 1/2004 | Sequin et al. | 623/1.12 |
| 2004/0015227 A1 | 1/2004 | Vardi et al. | 623/1.16 |
| 2004/0044396 A1 | 3/2004 | Clerc et al. | 623/1.13 |
| 2004/0059406 A1 | 3/2004 | Cully et al. | 623/1.11 |
| 2004/0088007 A1 | 5/2004 | Eidenschink | 607/1 |
| 2004/0117003 A1 | 6/2004 | Ouriel et al. | 623/1.35 |
| 2004/0133268 A1 | 7/2004 | Davidson et al. | 623/1.35 |
| 2004/0138732 A1 | 7/2004 | Suhr et al. | 623/1.11 |
| 2004/0138737 A1* | 7/2004 | Davidson et al. | 623/1.35 |
| 2004/0148006 A1 | 7/2004 | Davidson et al. | 623/1.11 |
| 2004/0172121 A1 | 9/2004 | Eidenschink et al. | 623/1.11 |
| 2004/0186560 A1 | 9/2004 | Alt | 623/1.35 |
| 2004/0225345 A1 | 11/2004 | Fischell et al. | 623/1.11 |
| 2004/0267352 A1* | 12/2004 | Davidson et al. | 623/1.11 |
| 2005/0010278 A1 | 1/2005 | Vardi et al. | 623/1.35 |
| 2005/0015108 A1 | 1/2005 | Williams et al. | 606/194 |
| 2005/0060027 A1 | 3/2005 | Khenansho et al. | 623/1.35 |
| 2005/0102021 A1 | 5/2005 | Osborne | 623/1.13 |
| 2005/0102023 A1* | 5/2005 | Yadin et al. | 623/1.15 |
| 2005/0119731 A1 | 6/2005 | Brucker et al. | 623/1.35 |
| 2005/0131526 A1 | 6/2005 | Wong | 623/1.15 |
| 2005/0149161 A1 | 7/2005 | Eidenschink et al. | 623/1.11 |
| 2005/0154442 A1 | 7/2005 | Eidenschink et al. | 623/1.11 |
| 2005/0154444 A1 | 7/2005 | Quadri | 623/1.13 |
| 2005/0183259 A1 | 8/2005 | Eidenschink et al. | 29/508 |
| 2005/0209673 A1 | 9/2005 | Shaked | 623/1.11 |
| 2005/0228483 A1 | 10/2005 | Kaplan et al. | 623/1.15 |
| 2006/0036315 A1* | 2/2006 | Yadin et al. | 623/1.35 |
| 2006/0041303 A1 | 2/2006 | Israel | 623/1.11 |
| 2006/0079956 A1 | 4/2006 | Eigler et al. | 623/1.35 |
| 2006/0173528 A1* | 8/2006 | Feld et al. | 623/1.15 |
| 2007/0055362 A1* | 3/2007 | Brown et al. | 623/1.35 |
| 2007/0073384 A1 | 3/2007 | Brown et al. | 623/1.16 |
| 2007/0100434 A1 | 5/2007 | Gregorich et al. | 623/1.16 |
| 2007/0118205 A1* | 5/2007 | Davidson et al. | 623/1.11 |
| 2007/0142902 A1* | 6/2007 | Yadin | 623/1.16 |
| 2007/0225796 A1* | 9/2007 | Yadin et al. | 623/1.16 |
| 2008/0065197 A1* | 3/2008 | Meyer et al. | 623/1.16 |
| 2008/0119925 A1* | 5/2008 | Yadin | 623/1.35 |
| 2008/0172123 A1* | 7/2008 | Yadin | 623/1.35 |
| 2008/0177377 A1* | 7/2008 | Meyer et al. | 623/1.35 |
| 2009/0076592 A1* | 3/2009 | Davidson et al. | 623/1.16 |
| 2009/0319030 A1* | 12/2009 | Yadin et al. | 623/1.35 |

FOREIGN PATENT DOCUMENTS

| | | |
|---|---|---|
| DE | 29701758 | 3/1997 |
| DE | 29701883 | 5/1997 |
| EP | 0479730 | 10/1991 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 0897700 | 7/2002 |
| EP | 0684022 | 2/2004 |
| EP | 1157674 | 7/2005 |
| EP | 1031330 | 11/2005 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/36709 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15109 | 4/1999 |
| WO | 99/24104 | 5/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 01/45594 | 6/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71055 | 11/2000 |
| WO | 00/74595 | 12/2000 |
| WO | 01/21095 | 3/2001 |
| WO | 01/21109 | 3/2001 |
| WO | 01/21244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |

(56) References Cited

FOREIGN PATENT DOCUMENTS

| WO | 01/89409 | 11/2001 |
|---|---|---|
| WO | 02/068012 | 9/2002 |
| WO | 03/055414 | 7/2003 |
| WO | 2004/026180 | 4/2004 |
| WO | 2005/009295 | 2/2005 |
| WO | 2005/014077 | 2/2005 |
| WO | 2005122959 | 12/2005 |

OTHER PUBLICATIONS

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

Caputo, Ronald P., "Stent Jail: A Minimum-Security Prison," *The American Journal of Cardiology*, vol. 77, pp. 1226-1230 (Jun. 1, 1996).

Colombo, M.D., Antonio, ""Kissing" Stent for Bifurcational Coronary Lesion," *Catheterization and Cardiovascular Diagnosis*, vol. 30, pp. 327-330 (Dec. 1993).

Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: To Treat or Not to Treat," *Catheterization and Cardiovascular Interventions*, vol. 50, pp. 411-412 (2000).

U.S. Appl. No. 09/663,111, filed Sep. 15, 2000, Davidson et al.

U.S. Appl. No. 09/614,472, filed Jul. 11, 2000, Davidson et al.

U.S. Appl. No. 09/325,996, filed Jun. 4, 1999, Vardi et al.

\* cited by examiner

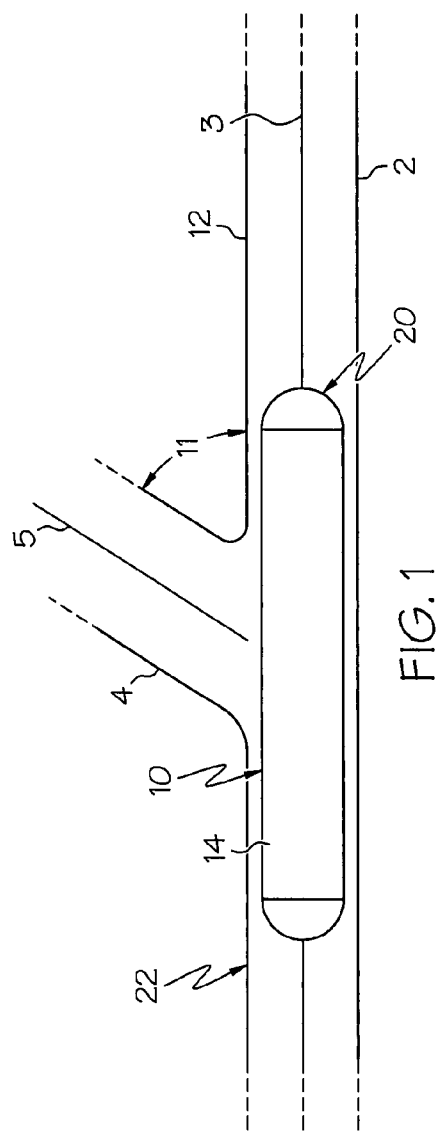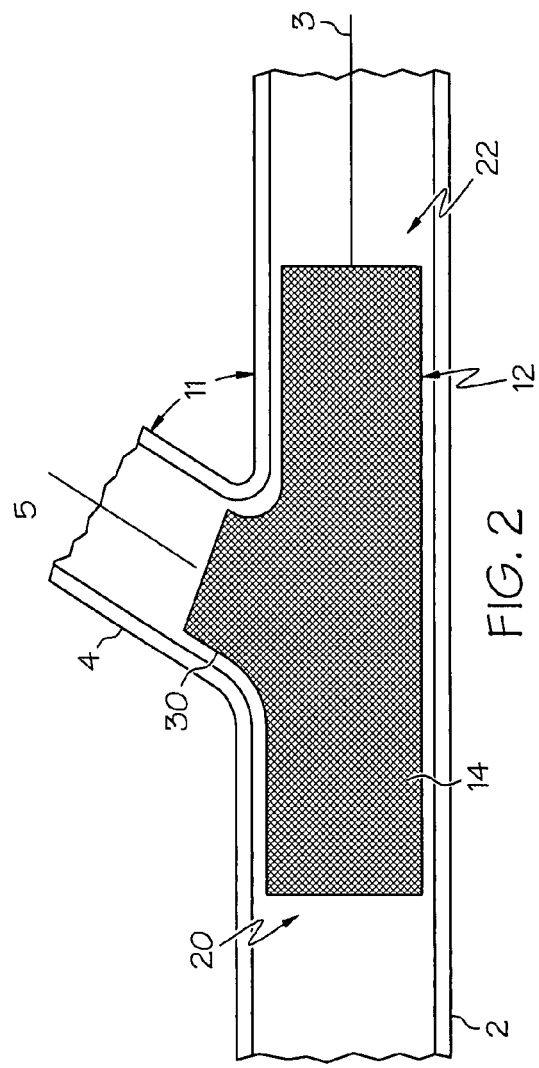

STENT WITH PROTRUDING BRANCH PORTION FOR BIFURCATED VESSELS

CROSS-REFERENCE TO RELATED APPLICATIONS

This application claims the benefit and is a continuation-in-part of U.S. patent application Ser. No. 11/010,730, filed Dec. 14, 2004, the entire contents of which is hereby incorporated herein by reference in its entirety.

BACKGROUND OF THE INVENTION

Stents, grafts, stent-grafts, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents can be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

There remains a need for novel stent designs that are suitable for use at a vessel bifurcation.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

In at least one embodiment, a stent comprises a plurality of interconnected framework members defining a plurality of cells. A portion of the interconnected framework members comprise a side branch structure defining an inner side branch cell that is shaped differently than other cells of the stent, the inner side branch cell having a side branch center point. The side branch structure comprises a first serpentine ring extending around the inner side branch cell, a second serpentine ring extending around the first serpentine ring and a plurality of side branch connectors. The first serpentine ring comprises a plurality of curved portions including convex curved portions that are convex with respect to the side branch center point, and concave curved portions that are concave with respect to the side branch center point. The convex curved portions include first convex curved portions and second convex curved portions, wherein the second convex curved portions are located farther away from a side branch center point than the first convex curved portions. Each side branch connector extends between a concave curved portion of the first serpentine ring and a portion of the second serpentine ring.

In at least one embodiment, a stent comprises a plurality of interconnected framework members defining a plurality of cells. A portion of the interconnected framework members comprise a side branch structure defining an inner side branch cell that is shaped differently than other cells of the stent, the inner side branch cell having a side branch center point. The side branch structure comprises a first serpentine ring extending around the inner side branch cell, a second serpentine ring extending around the first serpentine ring and a plurality of side branch connectors extending between the first serpentine ring and the second serpentine ring. The first serpentine ring comprises a plurality of curved portions including convex curved portions that are convex with respect to the side branch center point, and concave curved portions that are concave with respect to the side branch center point. The convex curved portions include first convex curved portions and second convex curved portions, wherein the second convex curved portions are located farther away from a side branch center point than the first convex curved portions. At least one side branch connector is connected to a second convex curved portion.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described a embodiments of the invention.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the invention may be embodied in practice.

In the drawings:

FIG. 1 is an illustration of a blood vessel bifurcation and an unexpanded stent mounted on an exemplary stent delivery system.

FIG. 2 is an illustration of the stent of FIG. 1 in an expanded condition.

DETAILED DESCRIPTION OF THE INVENTION

Figure 3:
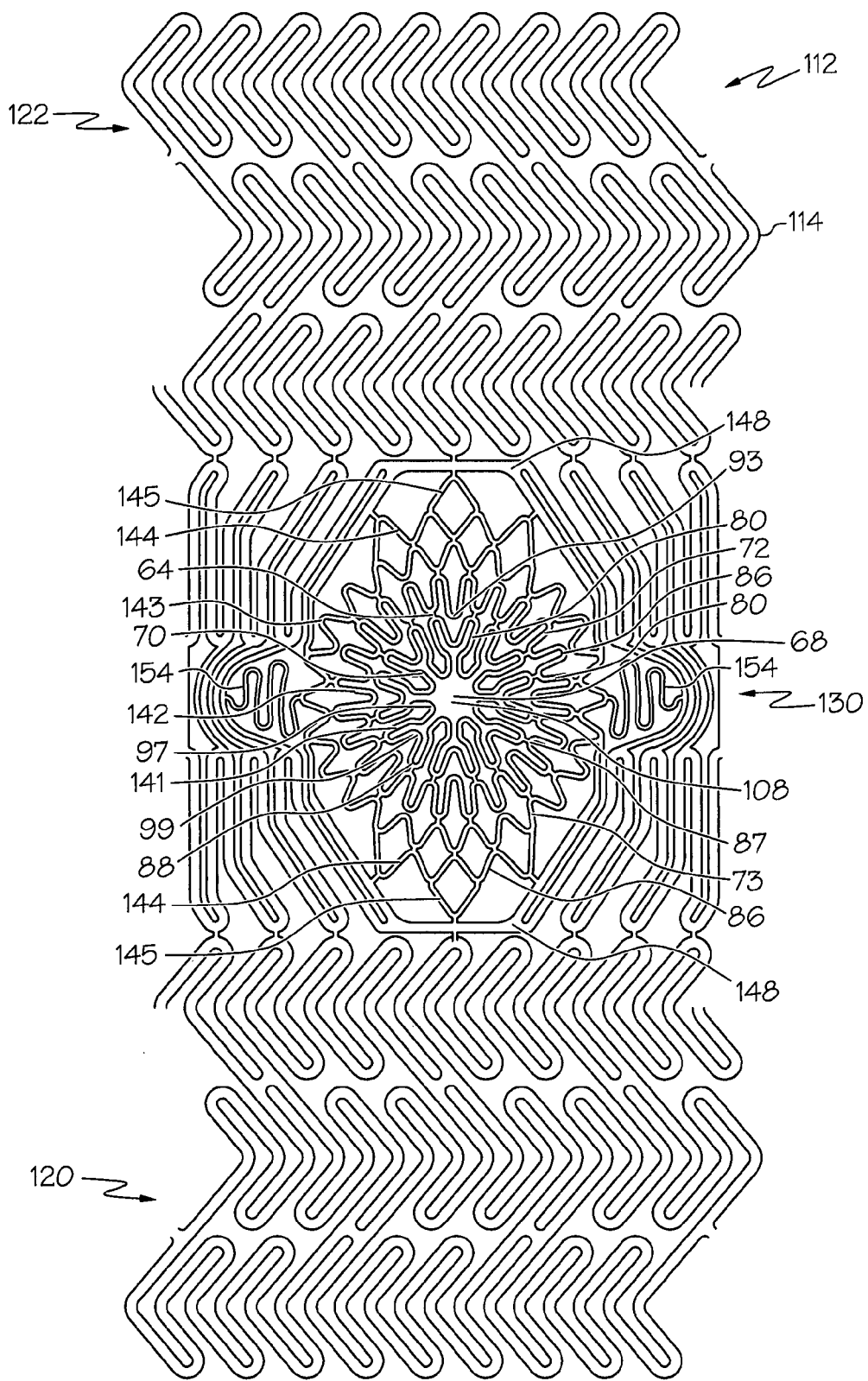
FIG. 3 is a flat view of an embodiment of an unexpanded stent in accordance with the present invention.

While this invention may be embodied in many different forms, there are described in detail herein specific embodiments of the invention. This description is an exemplification of the principles of the invention and is not intended to limit the invention to the particular embodiments illustrated.

The entire disclosures of U.S. Pat. No. 5,922,021, U.S. Pat. No. 6,123,721, U.S. Pat. No. 6,334,870, U.S. Pat. No. 6,478,816, U.S. Pat. No. 6,348,065, U.S. Pat. No. 6,325,826 and U.S. 2002-0095208 are hereby incorporated herein by reference in their entireties. The entire disclosures of U.S. patent application Ser. Nos. 10/802,036, 10/705,247, 10/644,550, 11/262,692, 11/519,552 and 60/844,011 are hereby incorporated herein by reference in their entireties.

For the purposes of this disclosure, like reference numerals in the figures shall refer to like features unless otherwise indicated.

Referring to FIGS. 1 and 2, an exemplary bifurcated blood vessel and bifurcated stent, in accordance with the principles of the invention, are shown. The vessel has a main vessel 2 and a branch vessel 4. Main vessel 2 and branch vessel 4 are disposed at an angle 11, which can be any angle but is shown as an angle of less than 90 degrees by way of example. With reference to FIG. 1, bifurcated stent 12 is shown in an unexpanded condition in FIG. 1. FIG. 2 shows stent 12 in an expanded configuration where branch portion 30 is outwardly deployed from the stent main portion as shown in a representative expanded state in the vasculature.

Stent 12 according to one embodiment of the present invention comprises stent body or wall 14 extending along a longitudinal axis 3 from a proximal end 20 to a distal end 22 and defining a lumen therein. Stent 12 may have a three-dimensional geometrical configuration having variable dimensions (length, width, height, depth, thickness, etc.). In a preferred embodiment, stent body 14 is a generally tubular structure. As defined herein, "tubular" can include an elongate structure that has varied cross-sections and does not require that the cross-section be circular. For example, the cross-section of stent wall 14 may be generally oval. In an alternate embodiment, stent body 14 is generally cylindrical. Also, the stent body 14 may have varied cross-sectional shapes along the longitudinal axis 3 of the stent. For example, the circumferences in the proximal and distal parts of the stent may be different. This may occur, for example, if during stent delivery the delivery system causes the stent to distend. A lumen represents the inner volumetric space bounded by stent body. In a preferred embodiment, stent 12 is radially expandable from an unexpanded state to an expanded state to allow the stent to expand radially and support the main vessel. In the unexpanded state, the stent body defines a lumen having a first volume, and in the expanded state, as illustrated in FIG. 1, the stent body defines a lumen having a second volume larger than the first volume.

FIG. 3 shows stent 112 in an unexpanded state in a flattened elevational view. Stent body 114 has a generally cellular configuration and comprises a generally repeatable series of struts and connectors configured in a predetermined general, overall, or main pattern at the proximal 122 and distal 120 ends of stent 12. Many other strut and connector patterns may be used, and the present pattern is shown for illustration purposes only.

Figure 4:
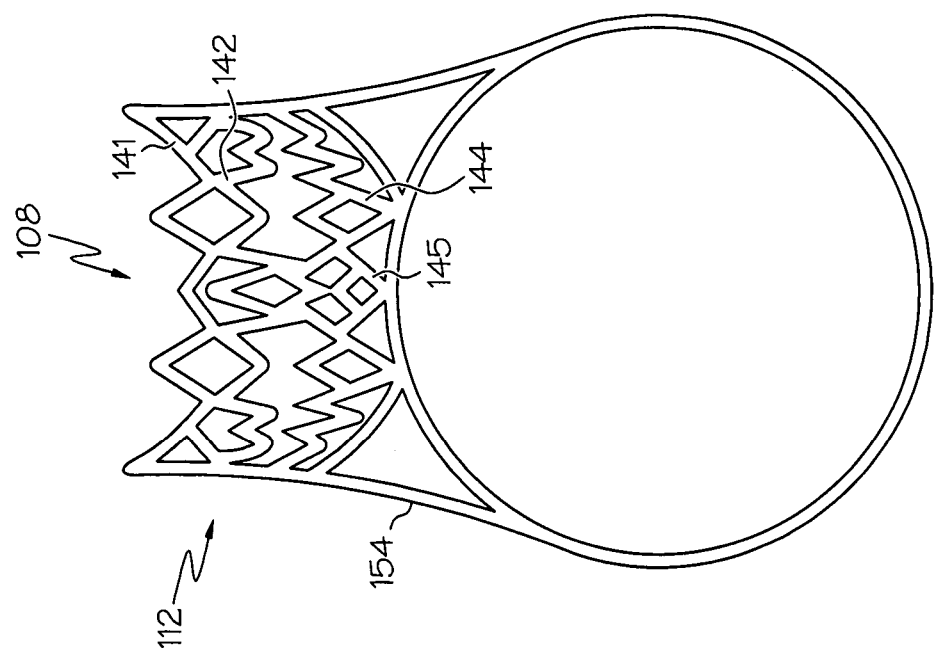
FIG. 4 is an end view of the stent in FIG. 3 in the expanded condition.

Stent 112 further includes a branch portion 130 located at some point along the length of stent 112. Branch portion 130 comprises a section or portion of stent wall 114 that is configured to extend into a branch vessel in a vessel bifurcation as discussed above. In general, branch portion 130 is configured to be movable from an unextended position to an extended position. In the unextended position, branch portion 130 is disposed in the volume defined by the unexpanded stent 112, that is, the branch portion 130 does not protrude radially from stent wall 114 as illustrated in FIG. 1. In the extended position, the branch portion 130 extends outwardly from stent wall 114 and branch portion 130 is extended into the branch vessel as illustrated in FIGS. 2 and 4. Branch portion 130 comprises a stent wall section of stent body 114 that is initially flush, coplanar, or cocylindrical with the remainder of stent body 114 and may extend outwardly with respect to the remainder of stent body 114. This configuration allows for access into a branch vessel, and at the same time allows for circumferential alignment of the stent within the vessel prior to deployment. In other embodiments, multiple branch portions can be incorporated into the stent to permit multiple access to one or more vessels. In a preferred embodiment, branch portion 130 may be positioned in the midsection of stent 112. In alternate embodiments, branch portion 130 may be positioned anywhere along the length of stent 112.

The details of branch portion 130 will be discussed. Branch portion 130 includes three interconnected rings 141, 142 and 143. As shown, rings 141, 142 and 143 are concentric, but could be non-concentric. The inner ring 141 defines undulation petals, prongs, or peaks surrounding a central branch opening 108. Branch opening 108 provides access to the side branch vessel when stent 112 is in the unexpanded condition. In this embodiment, undulation peaks of inner ring 141 are configured differently from the other rings. Rings 142 and 143 are formed, generally, from undulating configurations as shown. The amount and particular configuration of the rings is provided to allow for expansion into the branch. When stent 112 is expanded, as shown in FIG. 4, branch portion 130 is extended into the branch vessel (not shown), causing the expandable rings 141, 142 and 143 to at least partially cover the inner surface of the branch vessel. Thus, in a preferred embodiment, the stent coverage in a portion of the branch vessel includes the full circumference of the inner branch vessel wall. Branch portion 130 may include an auxiliary access opening to provide access to the side branch vessel as described in U.S. application Ser. No. 10/802,036 filed Mar. 17, 2004. Also, in the branch portion 130 may be modified to accommodate markers. Rings 141, 142 and 143 can be interconnected by a plurality of inner connectors as shown.

Outer ring 143 is connected to elliptical transition members 148 as shown and outer connectors 154, which can be generally S-shaped, zigzag-shaped, or wavelike. In this regard, the wavelike shape of distal outer connectors may be deformed to a greater extent and accommodate more expansion than, for example, a straight outer connector design. Outer ring 143 can be connected to partial rings 144 and 145 at the proximal and distal ends of stent 112. Partial ring 144 as shown has four undulations and ring 145 has one. These additional partial rings provide for a lattice configuration at the proximal and distal portion of the branch structure improving coverage thereat. Thus, with this configuration, more coverage is provided when the stent is expanded. Also, with this configuration, varying degrees of coverage or radial support of the side branch vessel wall upon installation into a side branch vessel can be provided. In alternate embodiments, other geometries may be used.

The branch portion 130 protrudes into the branch vessel when the stent is fully expanded. FIG. 4 shows an end view of stent 112 in an expanded configuration. The branch portion upon expansion can extend into the branch vessel in different lengths depending upon the application. The amount of extension may vary in a range between about 0.1-10.0 mm. In one preferred embodiment, the length of extension is 1-3 mm. In another preferred embodiment, the length of extension is approximately 2 mm. In alternative embodiments, the amount of extension into the branch vessel may be variable for different circumferential segments of branch portion 130. As shown in each of the embodiments, the branch portion is approximately 2.5 mm in width and about 2.5-3.0 mm in length. However, the branch portion can be dimensioned to accommodate varying size branch vessels. The branch portion can be formed of any tubular shape to accommodate the branch vessel, including, oval or circular, for example.

Figure 5:
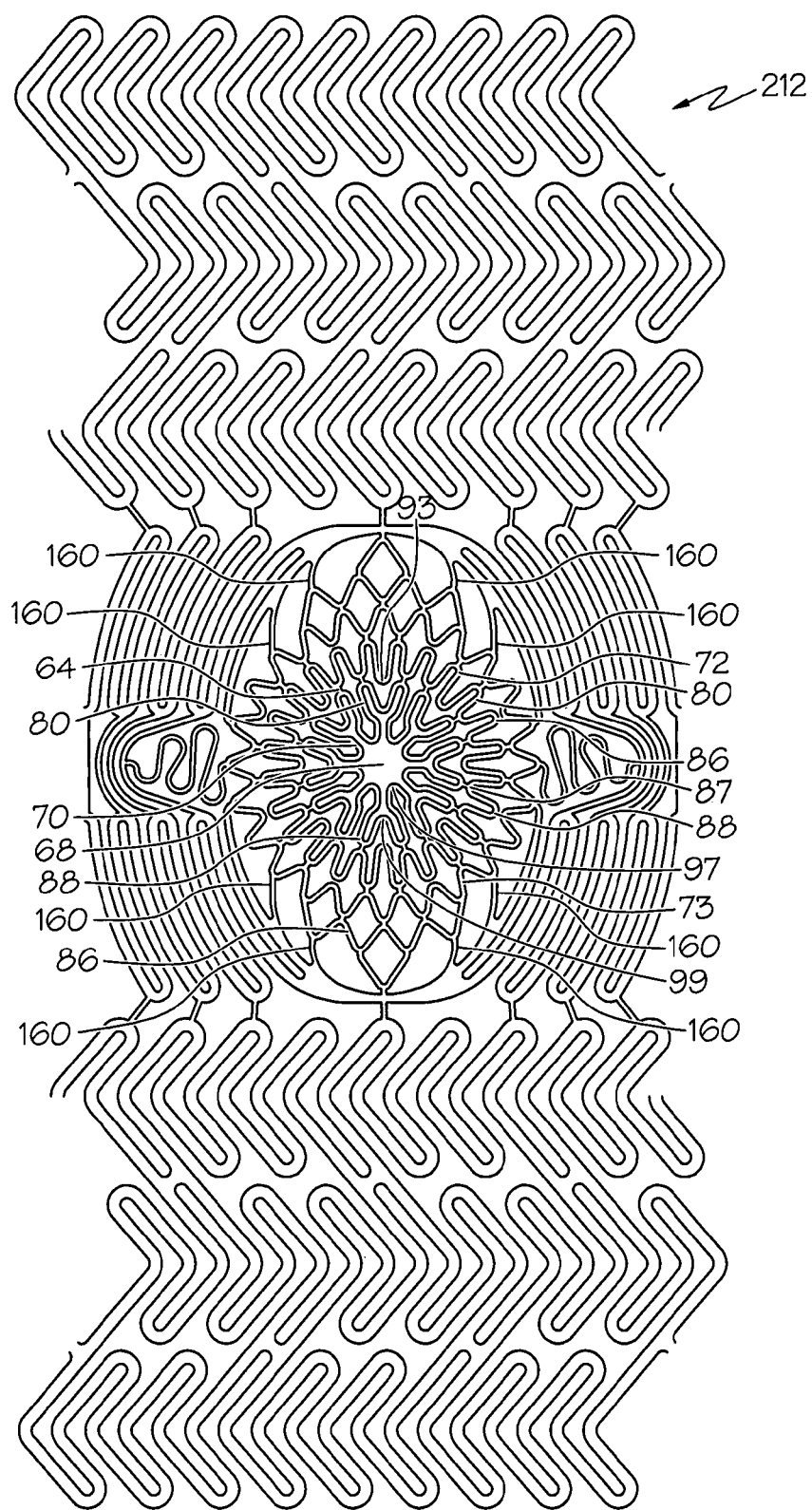
FIG. 5 is a flat view of another embodiment of an unexpanded stent in accordance with the present invention.

FIG. 5 shows an alternate embodiment of the stent shown in FIG. 3. In the embodiment of FIG. 5, stent 212 has substantially the same construction except that additional connectors 160 are provided. Connectors 160 provide additional coverage in the branch vessel.

Figure 6:
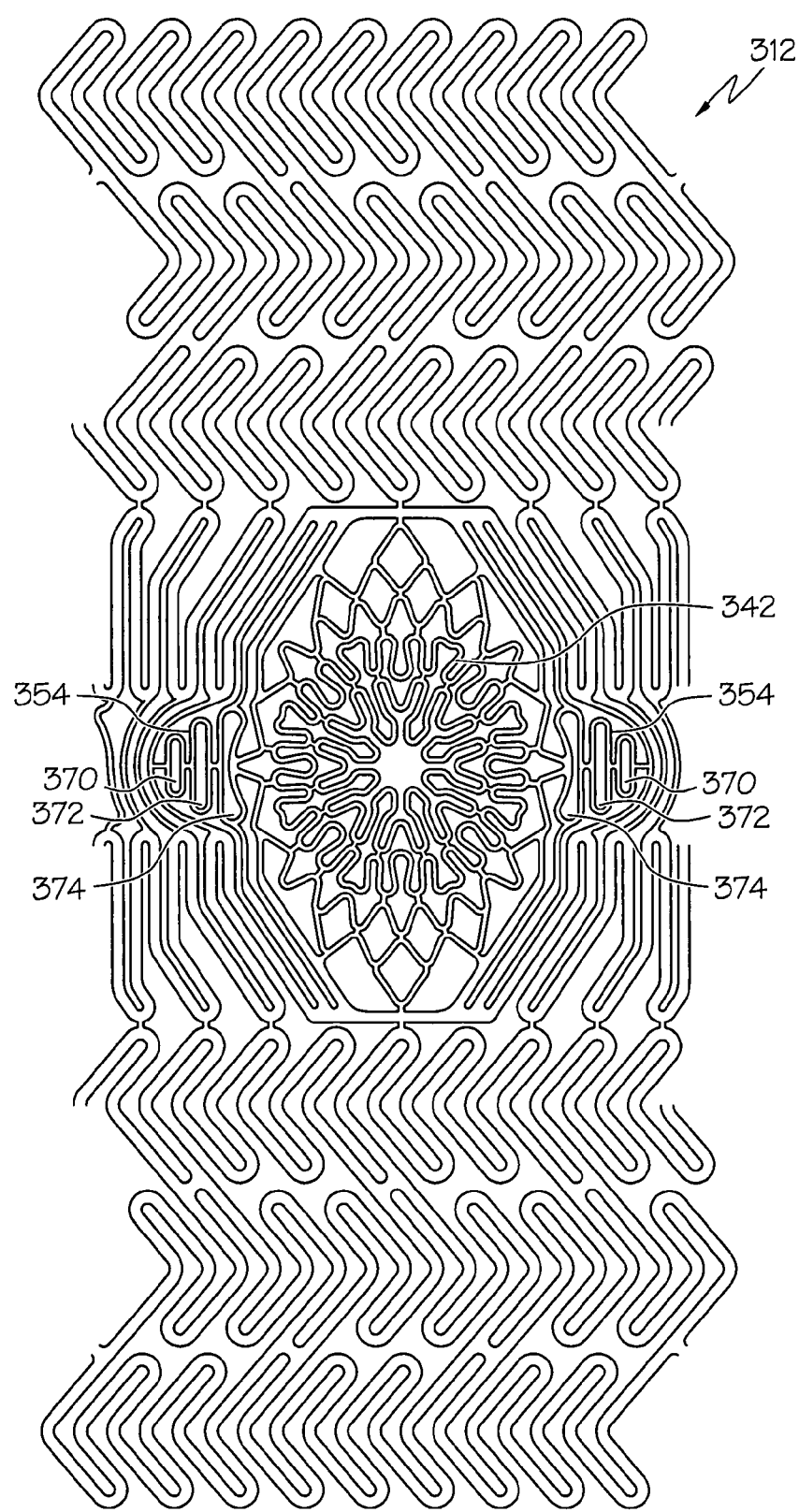
FIG. 6 is a flat view of another embodiment of an unexpanded stent in accordance with the present invention.

FIG. 6 shows an alternate embodiment of the stent shown in FIG. 3. In the embodiment of FIG. 6, stent 312 has substantially the same construction except that connectors 354 are different. Connectors 354 comprise a cellular structure each including three cells 370, 372 and 374. This cellular structure provides improved coverage and radial support. Additionally ring 342 includes a different pattern. Ring 342 has undulations with certain peaks modified to improve coverage.

In general, a wide variety of delivery systems and deployment methods may be used with the aforementioned stent embodiments. For example, a catheter system may be used for insertion and the stent may be balloon expandable or self-expandable, or the stent may be balloon expandable and the branch portion self-expandable, or vice versa. Once the stent is in position in the main vessel and the branch portion is aligned with the side branch the stent can be expanded. If the stent is balloon expandable, the stent may be expanded with a single expansion or multiple expansions. In particular, the stent can be deployed on a stent delivery system having a balloon catheter and side sheath as described, for example, in U.S. Pat. Nos. 6,325,826 and 6,210,429, the entire contents of which are incorporated herein by reference. In one preferred embodiment, a kissing balloon technique may be used, whereby one balloon is configured to expand the stent and the other balloon is configured to extend the branch portion. After the main portion of the stent is expanded in the main vessel, the stent delivery system may be removed and a second balloon may be passed through the side hole in the branch portion and expanded to expand the branch portion of the stent. In an alternate embodiment, the same balloon may be inserted in the main vessel inflated, deflated, retracted and inserted into the branch vessel, and then reinflated to expand the branch portion and cause it to protrude into the branch vessel. Alternatively, the stent can be delivered on two balloons and the main portion and the branch portion can be expanded simultaneously. As needed, the branch portion can be further expanded with another balloon or balloons. Yet another alternative is to use a specially shaped balloon that is capable of expanding the main and branch portions simultaneously. The stent can also be deployed with other types of stent delivery systems. Alternatively, the stent, or portions of the stent, can be made of a self-expanding material, and expansion may be accomplished by using self-expanding materials for the stent or at least the branch portion thereof, such as Nitinol, or by using other memory alloys as are well known in the prior art.

The construction and operation of catheters suitable for the purpose of the present invention are further described in U.S. patent application Ser. No. 09/663,111, filed Sep. 15, 2000, U.S. patent application Ser. No. 10/834,066, filed Apr. 29, 2004, and U.S. patent application Ser. No. 10/893,278, filed Jul. 19, 2004, the disclosures of which are incorporated herein by reference. It should be noted that the catheters taught in the above applications are exemplary, and that other catheters that are suitable with the stents of the subject application are included within the scope of the present application. In alternative embodiments, catheters without balloons may be used. For example, if the stent is comprised of memory alloy such as Nitinol, or is a mechanically self-expanding stent, balloons are not necessarily included on the catheters. Furthermore, any other catheter, including ones that are not disclosed herein, may be used to position stents according to the present invention.

Figure 7:
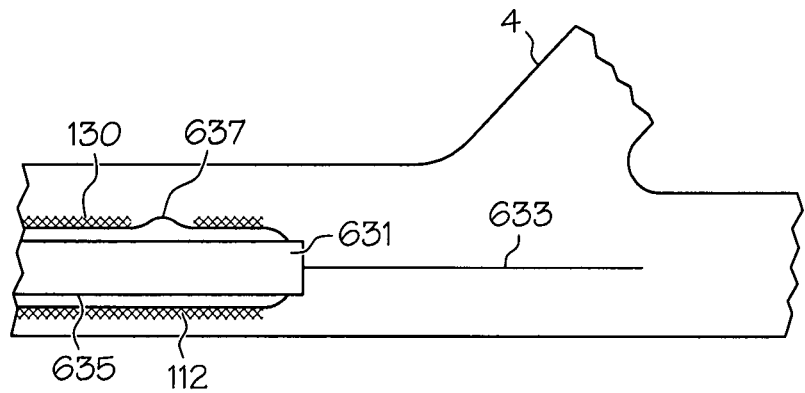
FIGS. 7-9 are illustrations of the steps for a method of inserting a stent of the present invention according to one embodiment of the invention.
Figure 8:
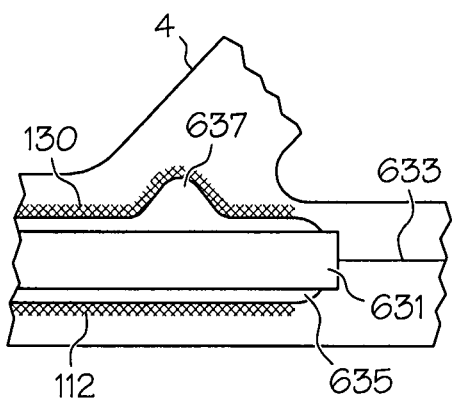
Figure 9:
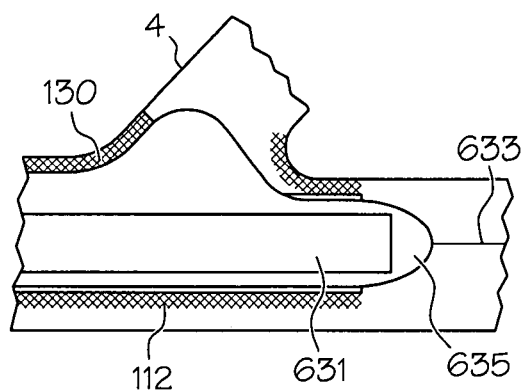

Referring now to FIGS. 7-9, illustrations of the steps of a method for employing a stent of the present invention is shown. By way of example, the method is depicted utilizing stent 112. The depicted method may be accomplished using a catheter system having a main catheter 631 including a herniated balloon 635 (FIG. 9). In particular, the stent can be deployed on a stent delivery system having a herniated balloon as described, for example, in U.S. patent application Ser. No. 10/834,066, the entire contents of which are incorporated herein by reference. As shown in FIG. 7, the catheter 631 includes a balloon 635 that has a protruding portion 637 that, upon expansion, protrudes outwardly from the cylindrical outer surface of the balloon causing the branch portion 130 to be extended into branch vessel 4.

Referring again to FIGS. 7-9, protruding portion 637 may be configured to fit directly into an opening in the stent. As shown in FIG. 7, catheter 631 is advanced over a guidewire 633 and positioned proximal to the bifurcation. As shown in FIG. 8, the catheter is advanced until the protruding portion 637 of the balloon is positioned at the bifurcation. In one embodiment, protruding portion 637 protrudes outwardly from catheter 631 enough so that it actually comes into contact with the bifurcation, thus providing a method of alignment with the branch vessel 4. Finally, as shown in FIG. 9, balloon 635 is expanded, which simultaneously causes the stent to expand and branch portion 130 to be pushed toward the branch vessel 4. Upon inflation of the balloon, the herniated portion 637 expands and extends through the branch portion 130 toward the side branch to open the entrance of the occluded side branch artery.

In an alternative method, the stent can be delivered using a herniated balloon and a dual lumen delivery system. This system can include a main catheter defining a first lumen with concentric guidewire lumen and balloon inflation lumen, a herniated balloon, as described above, on the main catheter, a side sheath with a guidewire lumen, and a stent. The stent is crimped over the main catheter, balloon and side sheath with the side sheath exiting the stent through a branch opening or side hole. The distal end of the side sheath is used for aligning the stent branch opening with the branch vessel 4.

The appendage or herniation may be located on a second catheter or side sheath of the delivery system, such as the system or as a bifurcated or split herniated balloon as described in U.S. patent application Ser. No. 10/834,066, and U.S. patent application Ser. No. 10/893,278, which are incorporated herein by reference.

FIGS. 10, 14, 15, 19-21 and 23 each show a flat pattern for another embodiment of a stent 12. Each stent 12 comprises a proximal end 20, a distal end 22 and a plurality of serpentine bands 18. For the purposes of this disclosure, like reference numerals in the figures shall refer to like features unless otherwise indicated.

In some embodiments, each serpentine band 18 comprises a plurality of struts 19. Circumferentially adjacent struts 19 within a serpentine band 18 are connected by turns 28. Turns 28 that point toward the proximal end 20 of the stent 12 comprise proximal peaks 24, and turns 28 that point toward the distal end 22 of the stent 12 comprise distal valleys 26. Each serpentine band 18 extends about at least a portion of the circumference of the stent 12.

A stent 12 can have any suitable number of serpentine bands 18. In various embodiments, a serpentine band 18 can have any suitable number of struts 19 and any suitable number of turns 28. In some embodiments, a serpentine band 18 can have a constant wavelength $\lambda$ or distance between repeating elements of the serpentine band 18. For example, a wavelength $\lambda$ may comprise a distance between adjacent proximal peaks 24 of a serpentine band 18, or a distance between adjacent distal valleys 26 of a serpentine band 18. In some embodiments, the wavelength $\lambda$ can change between adjacent serpentine bands 18. For example, the wavelength $\lambda$ of various serpentine bands 18 may be the shortest for serpentine bands 18 located near the center of the stent 12, and may increase as the stent 12 is traversed toward either end 12, 14. In some embodiments, a serpentine band 18 may have multiple portions, where each portion comprises a different wavelength $\lambda$.

A serpentine band 18 can span any suitable distance along the length of the stent 12. In some embodiments, the proximal peaks 24 of a given serpentine band 18 can be aligned about a circumference of the stent 12, and the distal valleys 26 can be similarly aligned about another circumference of the stent 12. In some embodiments, various peaks 24 may be offset from other peaks 24 within a given serpentine band 18, and various valleys 26 may be offset from other valleys 26 within the band 18.

Each strut 19 comprises a width, which can be measured in a direction normal to the length of the strut 19. In some embodiments, all struts 19 within a given serpentine band 18 have the same width. In some embodiments, the width of various struts 19 within a serpentine band 18 can change. In some embodiments, the width of struts 19 of one serpentine band 18 can be different from the width of struts 19 of another serpentine band 18.

Each turn 28 has a width, which can be measured in a direction normal to the side of the turn 28 (i.e. normal to a tangent line). In some embodiments, the width of a turn 28 can be greater than the width of one or more struts 19 of the stent 12. In some embodiments, the width of a turn 28 may be less than the width of one or more struts 19 of the stent 12. In some embodiments, the width of a turn 28 may vary from one end of the turn 28 to the other. For example, a turn 28 may connect to a strut 19 at one end having the same width as the strut 19. The width of the turn 28 may increase, and in some embodiments may reach a maximum at a midpoint of the turn 28. The width of the turn 28 may then decrease to the width of another strut 19, which may be connected to the second end of the turn 28.

In some embodiments, for example as shown in FIGS. 10, 14, 15, 19-21 and 23, serpentine bands 18 that are adjacent to one another along the length of the stent 12 are connected by at least one connector strut 16. In some embodiments, a connector strut 16 spans between turns 28 of adjacent serpentine bands 18. For example, one end of a connector strut 16 can connect to a distal valley 26 of one serpentine band 18, and the other end of the connector strut 16 can connect to a proximal peak 24 of an adjacent serpentine band 18.

Connector struts 16 can connect to any portion of a serpentine band 18, such as a turn 28, or in some embodiments, a strut 19. In some embodiments, a connector strut 16 is linear or straight along its length. In some embodiments, a connector strut 16 can include curvature along its length, can further include multiple portions of curvature, for example a convex portion and a concave portion that may be connected at an inflection point.

In some embodiments, a stent 12 comprises a first type of connector strut 36 and a second type of connector strut 38. A first connector strut 36 may extend in a first direction. The first connector strut 36 may be oriented at a first angle to a stent lengthwise axis 3. A second connector strut 38 may extend in a second direction that is different than or nonparallel to the first direction. In some embodiments, the first angle and the second angle may have the same magnitude but different orientations. For example, a first connector strut 36 may form a 70° angle with a stent lengthwise axis 3, while a second connector strut 38 may form a negative 70° angle with the stent lengthwise axis 3. In some embodiments, a first angle may comprise a mirror image of a second angle across a line parallel to the stent lengthwise axis 3.

A stent 12 further comprises a plurality of cells 37. A cell 37 comprises an opening in the stent 12 between the structural framework elements, such as serpentine bands 18 and connector struts 16. In some embodiments, a cell 37 may be bounded by a serpentine band 18, a connector strut 16, another serpentine band 18 and another connector strut 16.

In some embodiments, for example as shown in at least FIGS. 10, 14, 15, 19-21, a stent 12 comprises a first end region 50, a central region 52 and a second end region 54. Each region 50, 52, 54 extends across a portion of the length of the stent 12. Each region 50, 52, 54 includes a plurality structural framework elements, for example a plurality of serpentine bands 18. In some embodiments, all of the serpentine bands 18 within a given region 50, 52, 54 are similar in size and shape. In some embodiments, various serpentine bands 18 within a given region 50, 52, 54 may be different in size, shape, strut width, wavelength λ, etc. For example, in some embodiments, serpentine bands 18 located in the central region 52 span a greater distance along the length of the stent 12 than serpentine bands 18 located in the end regions 50, 54. In some embodiments, the struts 19 of serpentine bands 18 located in the central region 52 have a greater length than struts 19 located in the end regions 50, 54. In some embodiments, the struts 19 of serpentine bands 18 located in the end regions 50, 54 are wider than struts 19 located in the central region 52. In some embodiments, the wavelength λ of serpentine bands 18 located in the central region 52 is less than the wavelength λ of serpentine bands 18 located in the end regions 50, 54.

In some embodiments, an area of the stent 12 located between two adjacent serpentine bands 18 can be considered a connector column 44. Each connector column 44 comprises a plurality of connector struts 16. In some embodiments, each connector strut 16 in a connector column 44 can be similar to one another. For example, each connector strut 16 in a first connector column 44*a* can comprise a first type of connector strut 36. Each connector strut 16 in a second connector column 44*b* can comprise a second type of connector strut 38.

In some embodiments, first connector columns 44*a* and second connector columns 44*b* can alternate along the length of the stent 12. Thus, each interior serpentine band 18 can be positioned between a first connector column 44*a* and a second connector column 44*b*. Accordingly, connector struts 16 that connect to one side of a serpentine band 18 can comprise first connector struts 36, and connector struts 16 that connect to the other side of the serpentine band 18 can comprise second connector struts 38.

Turns 28 can comprise connected turns 58 or unconnected turns 55 depending upon whether the turn 28 connects to a connector strut 16.

A serpentine band 18 can have more unconnected turns 55 than connected turns 58. In some embodiments, a serpentine band 18 has three unconnected turns 55 for each connected turn 58. The 3:1 ratio of unconnected turns 55 to connected turns 58 can also apply to the proximal peaks 24 and to the distal valleys 26.

In some embodiments, for example as shown in at least FIGS. 10, 11, 14, 15, 19-21, the central region 52 further comprises a side branch structure 60 and a side branch support ring 42. In some embodiments, the support ring 42 can be considered a portion of the side branch structure 60. In various embodiments, some or all of the serpentine bands 18 located in the central region 52 extend about a portion of the stent circumference, while the remainder of the circumference is occupied by the side branch structure 60 and the support ring 42.

In some embodiments, serpentine bands 18 located in the central region 52 attach directly to a portion of the support ring 42.

In some embodiments, a serpentine band 18 comprises one or more shorter struts 32. A shorter strut 32 is generally shorter than other struts 19 of the serpentine band 18. Shorter struts 32 can be located in proximity to the side branch structure 60, and in some embodiments, a shorter strut 32 can connect to a portion of the side branch structure 60. A serpentine band 18 can also comprise one or more offset turns 34, which can connect to one or more shorter struts 32. An offset turn 34 is generally offset from other turns 28 of the serpentine band 18 that face the same direction (e.g. point toward the same direction). For example, most of the distal valleys 26 of a serpentine band 18 may be aligned about a reference circumference of the stent 12, while an offset distal valley 34 located in the same serpentine band 18 is not aligned on the aforementioned reference circumference.

In some embodiments, a serpentine band 18 can comprise one or more nonparallel struts 23, wherein the nonparallel strut 23 is not parallel to any other struts 19 of the serpentine band 18 when viewed as a flat pattern.

In various embodiments, serpentine bands 18 located in the central region 52 can comprise any suitable combination of struts 19 and turns 28, including struts of varying length, struts having curvature and turns having any suitable location and orientation.

The side branch structure 60 comprises structural elements that can displace outwardly from other portions of the stent 12, for example extending into a side branch vessel. The side branch structure 60 generally comprises a plurality of serpentine rings 62 and a plurality of side branch connectors 63.

Figure 10:
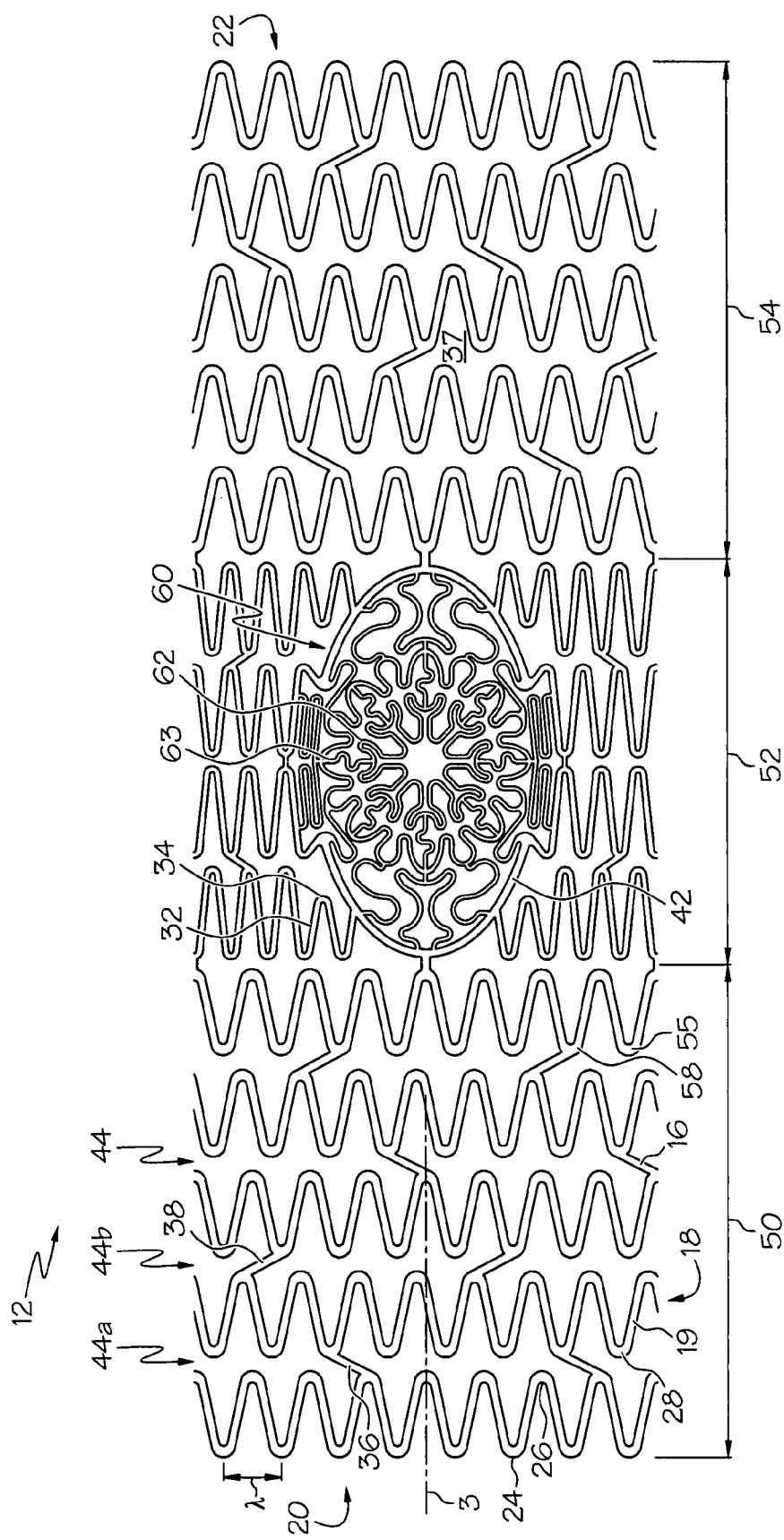
FIG. 10 shows a flat pattern for another embodiment of a stent.
Figure 11:
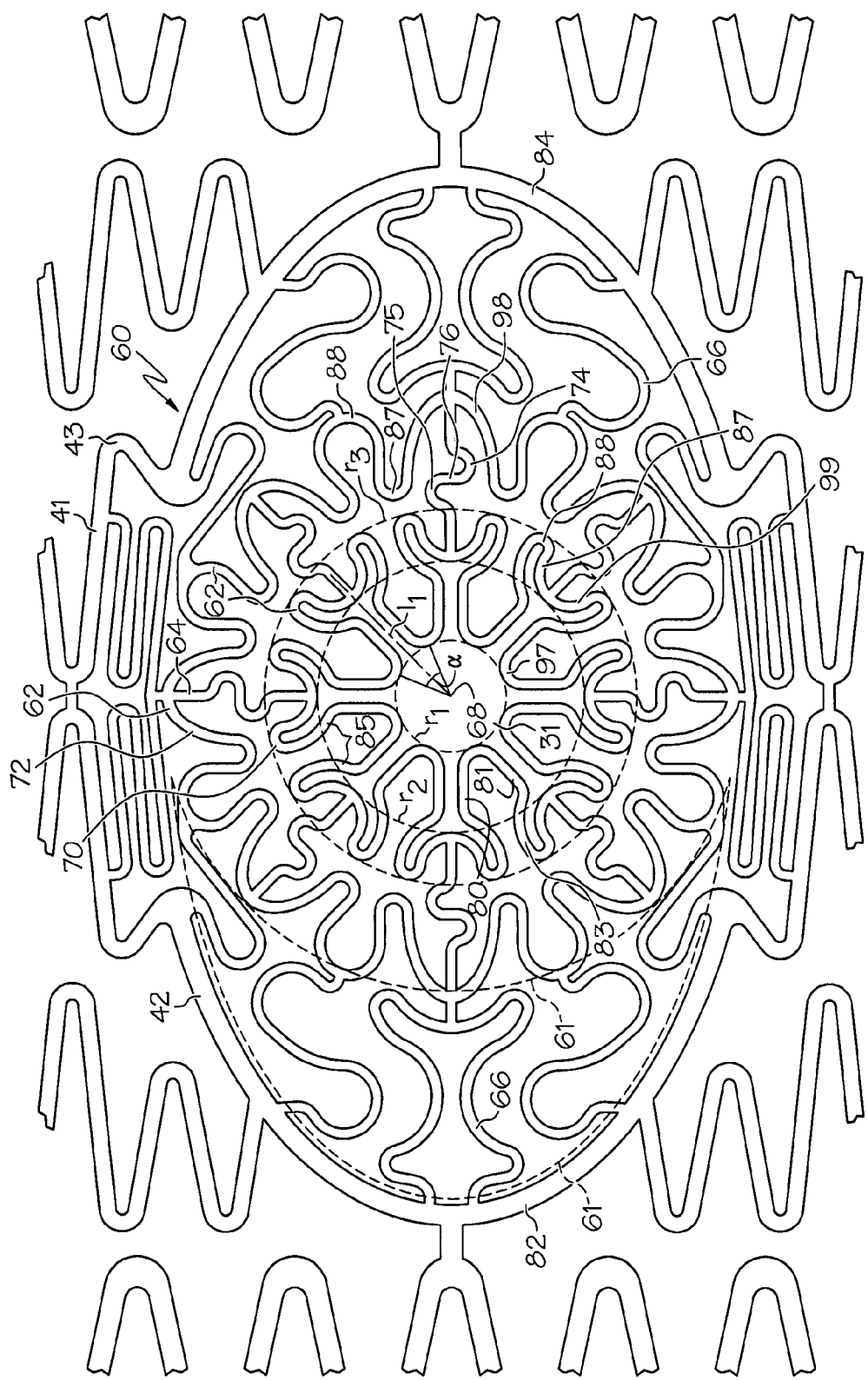
FIG. 11 shows a portion of the flat pattern of FIG. 10 in greater detail.

FIG. 11 shows the side branch structure 60 from the embodiment of FIG. 10 in greater detail.

In some embodiments, the side branch structure 60 comprises a first serpentine ring 70, a second serpentine ring 72 and plurality of side branch inner connectors 64. The serpentine rings 70, 72 are also referred to herein as side branch rings.

The first serpentine ring 70 extends around and defines an inner side branch cell 31. The inner side branch cell 31 can be shaped differently from all other cells 37 of the stent 12. A side branch center point 68 comprises the center of the inner side branch cell 31. In some embodiments, the side branch rings 70, 72 are centered upon the side branch center point 68.

In some embodiments, the first serpentine ring 70 comprises a plurality of curved portions 86. In some embodiments, a curved portion 86 comprises a constant radius of curvature. In some embodiments, a curved portion 86 can be centered in a side branch radial direction. Thus, a line oriented in a side branch radial direction that passes through the side branch center point 68 can bisect a curved portion 86. When a curved portion 86 is bisected by a line, a first half of the curve located on one side of the line comprises a mirror image of a second half of the curve located on the other side of the line.

In some embodiments, curved portions 86 of the first serpentine ring 70 can comprise convex curved portions 87 and concave curved portions 88. The convex curved portions 87 are convex with respect to the side branch center point 68, and the concave curved portions 88 are concave with respect to the side branch center point 68. In some embodiments, convex curved portions. 87 can generally point inward with respect to the side branch, for example pointing toward the side branch center point 68. In some embodiments, concave curved portions 88 can generally point outward with respect to the side branch, for example pointing away from the side branch center point 68.

In some embodiments, the peak of the convex curved portions 87 are generally located closer to the side branch center point 68 than the peak of the concave curved portions 88.

In some embodiments, the convex curved portions 87 can comprise first convex curved portions 97 and second convex curved portions 99.

In some embodiments, the first convex curved portions 97 are each located an equal distance away from the side branch center point 68, and thus can be considered aligned around a first reference circle $r_1$ centered upon the side branch center point 68. The first convex curved portions 97 can also be equally distributed around the circumference of the first reference circle $r_1$.

In some embodiments, the second convex curved portions 99 are each located an equal distance away from the side branch center point 68, and thus can be considered aligned around a second reference circle $r_2$ centered upon the side branch center point 68. The second convex curved portions 99 can also be equally distributed around the circumference of the second reference circle $r_2$. The second reference circle $r_2$ comprises a larger radius than the first reference circle $r_1$.

In some embodiments, the first convex curved portions 97 and the second convex curved portions 99 are collectively equally spaced around the side branch center point 68. Thus, a reference line $l_1$ oriented in a side branch radial direction that bisects a second convex curved portion 99 will bisect the angle α between two first convex curved portions 97. Similarly, a line that bisects a first convex curved portion 97 will bisect an angle formed between the two second convex curved portions 99 located on either side of the first convex curved portion 97.

In some embodiments, the second convex curved portions 99 span a greater distance than the first convex curved portions 97, wherein the ends of the second convex curved portions 99 are farther away from one another than the ends of the first convex curved portions 97.

In some embodiments, each first convex curved portion 97 of the first serpentine ring 70 comprises the same shape and has the same radius of curvature as all other first convex curved portion 97 of the first serpentine ring 70. In some embodiments, each second convex curved portion 99 of the first serpentine ring 70 comprises the same shape and has the same radius of curvature as all other second convex curved portion 99 of the first serpentine ring 70.

In some embodiments, each second convex curved portion 99 is connected at one end to a concave curved portion 88 and connected at the other end to another concave curved portion 88.

In some embodiments, the peaks of the concave curved portions 88 of the first serpentine ring 70 are each located an equal distance away from the side branch center point 68, and thus can be considered aligned around a third reference circle $r_3$ centered upon the side branch center point 68. The concave curved portions 88 can also be equally distributed around the circumference of the third reference circle $r_3$. The third reference circle $r_3$ comprises a larger diameter than the second reference circle $r_2$.

In some embodiments, the first serpentine ring 70 further comprises a plurality of struts 80. In some embodiments, each strut 80 can connect between a first convex curved portion 97 and a concave curved portion 88.

In some embodiments, a strut 80 comprises a straight portion 81. In some embodiments, a straight portion 81 can connect to a first convex curved portion 97.

In some embodiments, a strut 80 further comprises a bent portion 83. In some embodiments, a bent portion 83 can connect to a concave curved portion 88. In some embodiments, at least a portion of a bent portion 83 of a strut 80 can extend parallel to a second convex curved portion 99. In some embodiments, a radius of curvature of a bent portion 83 can have the same center point as a radius of curvature of a second convex curved portion 99.

In some embodiments, the first serpentine ring 70 comprises a plurality of strut pairs 85. Each strut pair 85 comprises two struts 80, wherein the struts 80 of the pair 85 are mirror images of one another taken across a side branch radial line that passes through the side branch center point 68, such as radial line $l_1$. In some embodiments, the struts 80 of a strut pair 85 are connected by a first convex curved portion 97. In some embodiments, the struts 80 of a strut pair 85 are connected by a combination of two concave curved portions 88 and a second convex curved portion 99.

In some embodiments, the first serpentine ring 70 comprises a repeating pattern of a first convex curved portion 97, a strut 80, a concave curved portion 88, a second convex curved portion 99, another concave curved portion 88 and another strut 80. In various embodiments, this pattern can be repeated a plurality of times, such as 4, 6, 8, 10 or 12 times.

The second serpentine ring 72 extends around the first serpentine ring 70. In some embodiments, the second serpentine ring 72 is coaxial with the first serpentine ring 70, and thus can be centered upon the side branch center point 68.

In some embodiments, the second serpentine ring 72 comprises alternating convex portions 87 and concave portions 88. Thus, the curved portions 86 located on either side of a convex curved portion 87 comprise concave curved portions 88, and the curved portions 86 located on either side of a concave curved portion 88 comprise convex curved portions 87. The convex curved portions 87 are generally located closer to the side branch center point 68 than the concave curved portions 88. In some embodiments, convex curved portions 87 point inward with respect to the side branch, for example pointing toward the side branch center point 68. In some embodiments, concave curved portions 88 point outward with respect to the side branch, for example pointing away from the side branch center point 68. In some embodiments, each convex portion 87 comprises a constant radius of curvature. In some embodiments, each convex portion 87 of the second serpentine ring 72 comprises the same radius of curvature.

In some embodiments, a concave portion 88 comprises a constant radius of curvature. In some embodiments, each concave portion 88 of the second serpentine ring 72 that has a constant radius of curvature comprises the same radius of curvature.

In some embodiments, a concave portion 88 comprises a parabolic shape 98. In some embodiments, every other concave portion 88 of the second serpentine ring 72 comprises a constant radius of curvature, and every other concave portion 88 comprises a parabolic shape 98.

In some embodiments, the first serpentine ring 70 and the second serpentine ring 72 can each be symmetrical across a side branch major axis that extends parallel to the stent longitudinal axis 3. In some embodiments, the first serpentine ring 70 and the second serpentine ring 72 can be symmetrical across a side branch minor axis that extends perpendicular to the stent longitudinal axis 3.

In some embodiments, a curved portion 86 of the second serpentine ring 72 can be aligned with a curved portion 86 of the first serpentine ring 70 in a side branch radial direction. Thus, a line oriented in a side branch radial direction that bisects a curved portion 86 of the first serpentine ring 70 can also bisect a curved portion 86 of the second serpentine ring 72. In some embodiments, a convex curved portion 87 of the first serpentine ring 70 can be aligned with a concave curved portion 88 of the second serpentine ring 72 in a side branch radial direction. In some embodiments, each convex curved portion 87 of the first serpentine ring 70 is aligned with concave curved portion 88 of the second serpentine ring 72 in a side branch radial direction. In some embodiments, each first convex curved portion 97 of the first serpentine ring 70 is aligned with a concave portion 88 of the second serpentine ring 72 that comprises a constant radius of curvature. In some embodiments, each second convex curved portion 99 of the first serpentine ring 70 is aligned with a concave portion 88 of the second serpentine ring 72 that comprises a parabolic shape 98.

In some embodiments, an inner connector 64 connects between the first serpentine ring 70 and the second serpentine ring 72. In some embodiments, an inner connector 64 is connected at an inner end to a curved portion 86 of the first side branch ring 70 and is connected at an outer end to a curved portion 86 of the second side branch ring 72. In some embodiments, an inner connector 64 spans between a second convex curved portion 99 of the first serpentine ring 70 and a concave curved portion 88 of the second serpentine ring 72. In some embodiments, an inner connector 64 spans between a second convex curved portion 99 of the first serpentine ring 70 and a concave curved portion 88 of the second serpentine ring 72 that comprises a parabolic shape 98.

In some embodiments, the number of inner connectors 64 is equal to the number of second convex curved portions 99 of the first serpentine ring 70.

In some embodiments, an inner connector 64 comprises an s-shape 75. In some embodiments, an inner connector 64 comprises at least one straight strut 76 and at least one turn 74. In some embodiments, a straight strut 76 of an inner connector 64 can be perpendicular to another straight strut 76 included in the same inner connector 64.

In some embodiments, the side branch structure 60 further comprises one or more side branch outer connectors 66. In some embodiments, a side branch outer connector 66 is connected at one end to the second serpentine ring 72 and is connected at the other end to another portion of the stent 12, such as a support ring 42 that extends around the side branch structure 60. In some embodiments, an outer connector 66 can be connected at each end to the support ring 42, and can also connect to a side branch ring 62, for example at a location along its length. In some embodiments, portions of the outer connector 66 on either side of the connection to the side branch ring 62 can comprise mirror images of one another.

In some embodiments, an outer connector 66 comprises a serpentine structure that can extend throughout a portion of an ancillary side branch area 61. In some embodiments, the ancillary side branch area 61 comprises area within the support ring 42 that is not occupied by the side branch rings 62.

In some embodiments, the support ring 42 extends around the side branch structure 60 and provides a more rigid support to the side branch structure 60 than would otherwise be provided by the serpentine bands 18 alone. In some embodiments, the support ring 42 comprises a substantially constant strut width, and in some embodiments, struts of the support ring 42 have a greater width than elements of the serpentine bands 18 or other side branch structure 60. In some embodiments, the struts of the support ring 42 have an average width that is greater than an average width of the struts 80 of the first side branch ring 70.

In some embodiments, the support ring 42 includes a first portion 82 and a second portion 84 located on axially opposed sides of the side branch structure 60. In some embodiments, the second portion 84 comprises a mirror image of the first portion taken across the side branch minor axis, which can be oriented in a stent circumferential direction and can pass through the side branch center point 68. In some embodiments, at least a portion of either portion 82, 84 can comprise a parabolic shape that is concave with respect to the side branch center point 68.

In some embodiments, the support ring 42 comprises a plurality of struts 41 and a plurality of turns 43. In some embodiments, a strut 41 can be parallel to a strut 19 of a serpentine band 18.

In some embodiments, the support ring 42 can also be described as extending around a portion of the side branch structure 60 and connecting to one or more serpentine band(s) 18, wherein the serpentine band(s) 18 extend around the remaining portion of the side branch structure 60.

In some embodiments, a portion of a serpentine band 18 can transition into a portion of the support ring 42. In some embodiments, a strut 41 of the support ring 42 can connect to a turn 28 of a serpentine band. In some embodiments, a turn 43 of the support ring 42 can connect to a strut 19 of a serpentine band 18.

Figure 12:
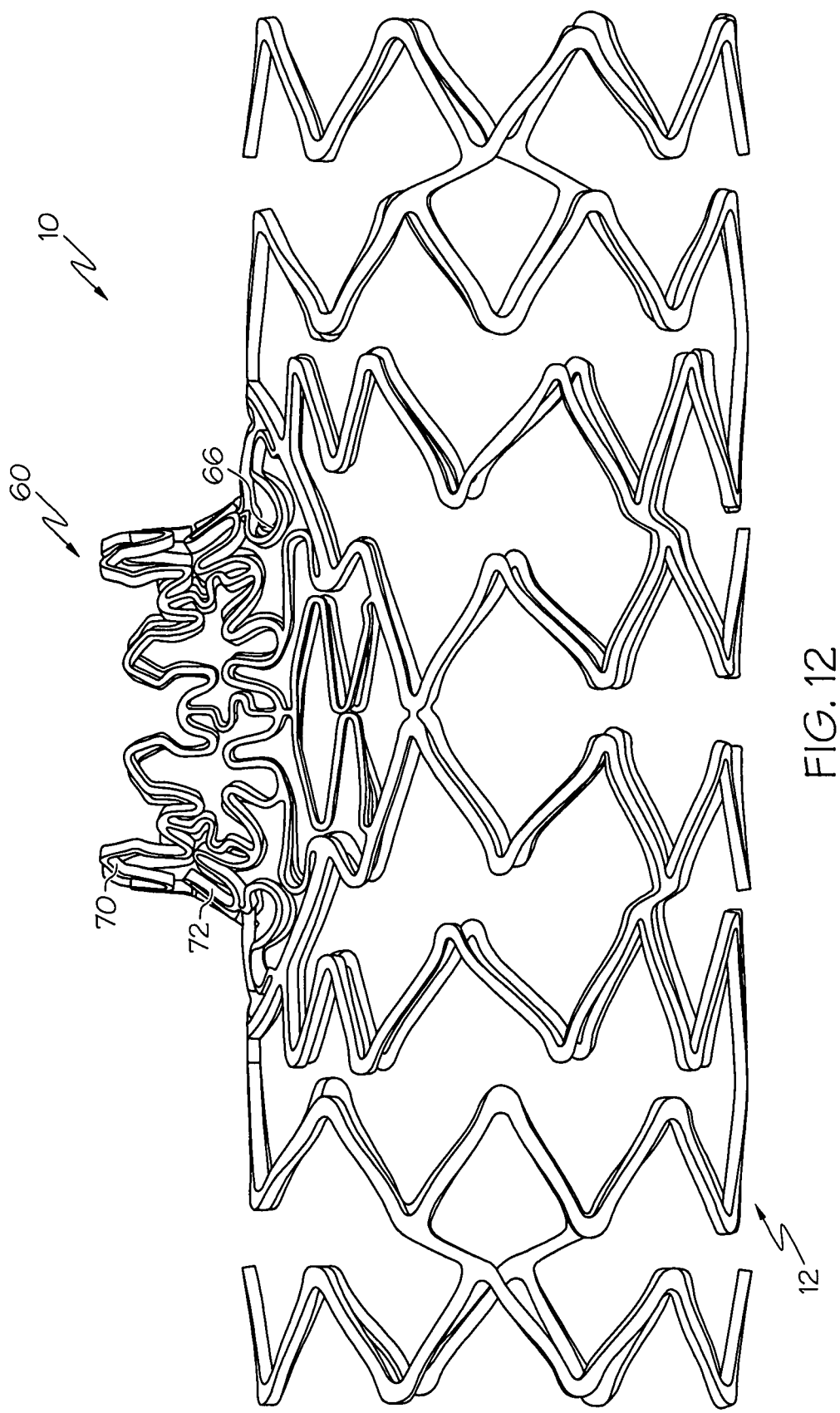
FIG. 12 shows a side view of a stent according to the flat pattern of FIG. 10.

FIG. 12 shows a side view of a stent according to the flat pattern of FIG. 10. The stent 12 is shown in an expanded configuration with the side branch structure 60 outwardly deployed. The second serpentine ring 72 extends outwardly from the generally cylindrical main stent 10 body. The first serpentine ring 70 has expanded in diameter and extends outwardly above the second serpentine ring 72.

Figure 13:
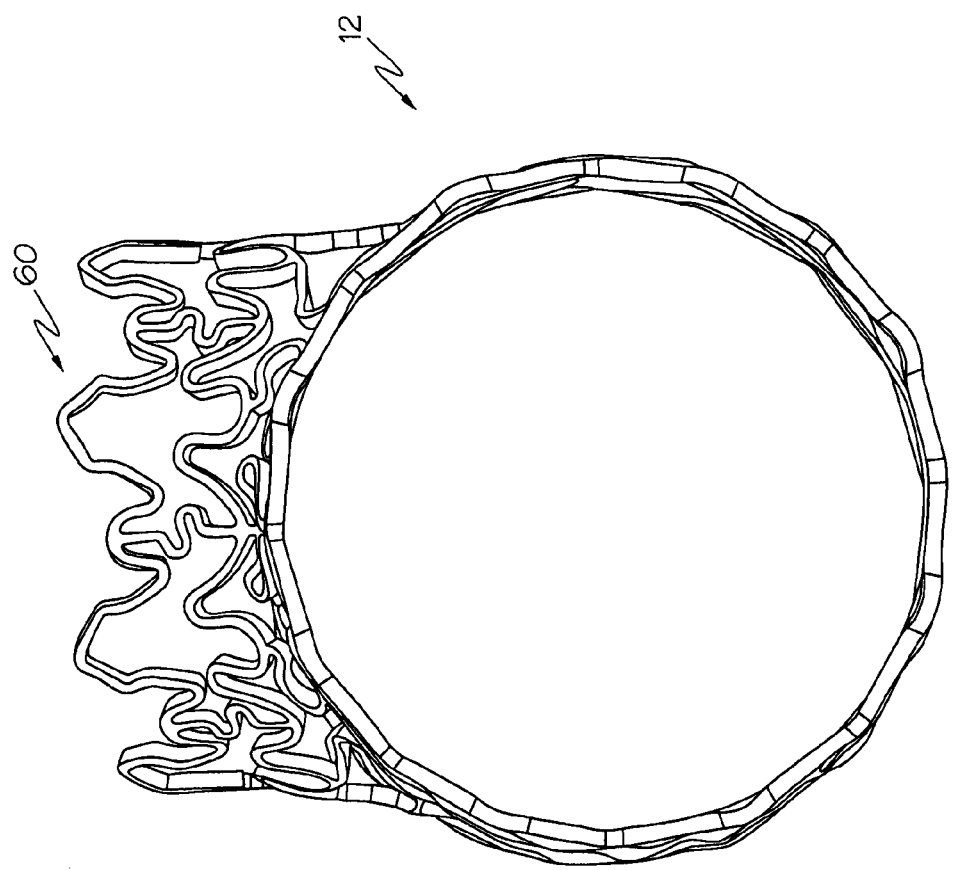
FIG. 13 shows an end view of a stent according to the flat pattern of FIG. 10.

FIG. 13 shows an end view of a stent according to the flat pattern of FIG. 10 in an expanded configuration with the side branch structure 60 outwardly deployed.

Figure 14:
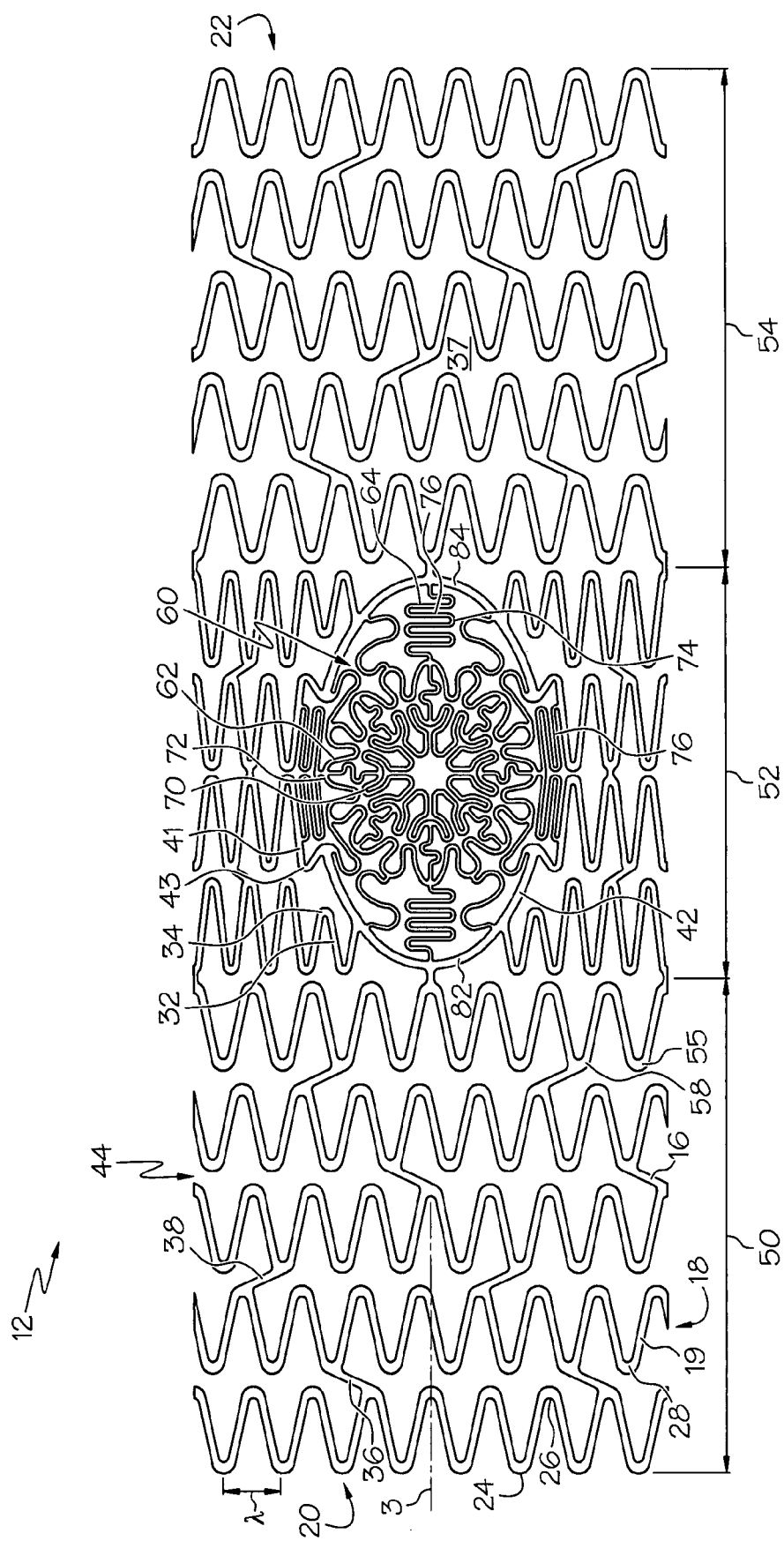
FIG. 14 shows a flat pattern for another embodiment of a stent.

FIG. 14 shows a flat pattern for another embodiment of a stent 12.

In some embodiments, an outer connector 66 can comprise a plurality of straight struts 76 and a plurality of turns 74. In some embodiments, a straight strut 76 of an outer connector 66 can be perpendicular to another straight strut 76 included in the same outer connector 66. In some embodiments, an outer connector 66 comprises a plurality of straight struts 76 that are parallel to one another.

In some embodiments, an outer connector 66 can be connected at one end to the support ring 42 and at the other end to a side branch ring 62. In some embodiments, an outer connector 66 can be connected at each end to the support ring 42, and can also connect to a side branch ring 62. In some embodiments, portions of the outer connector 66 on either side of the connection to the side branch ring 62 can comprise mirror images of one another.

Figure 15:
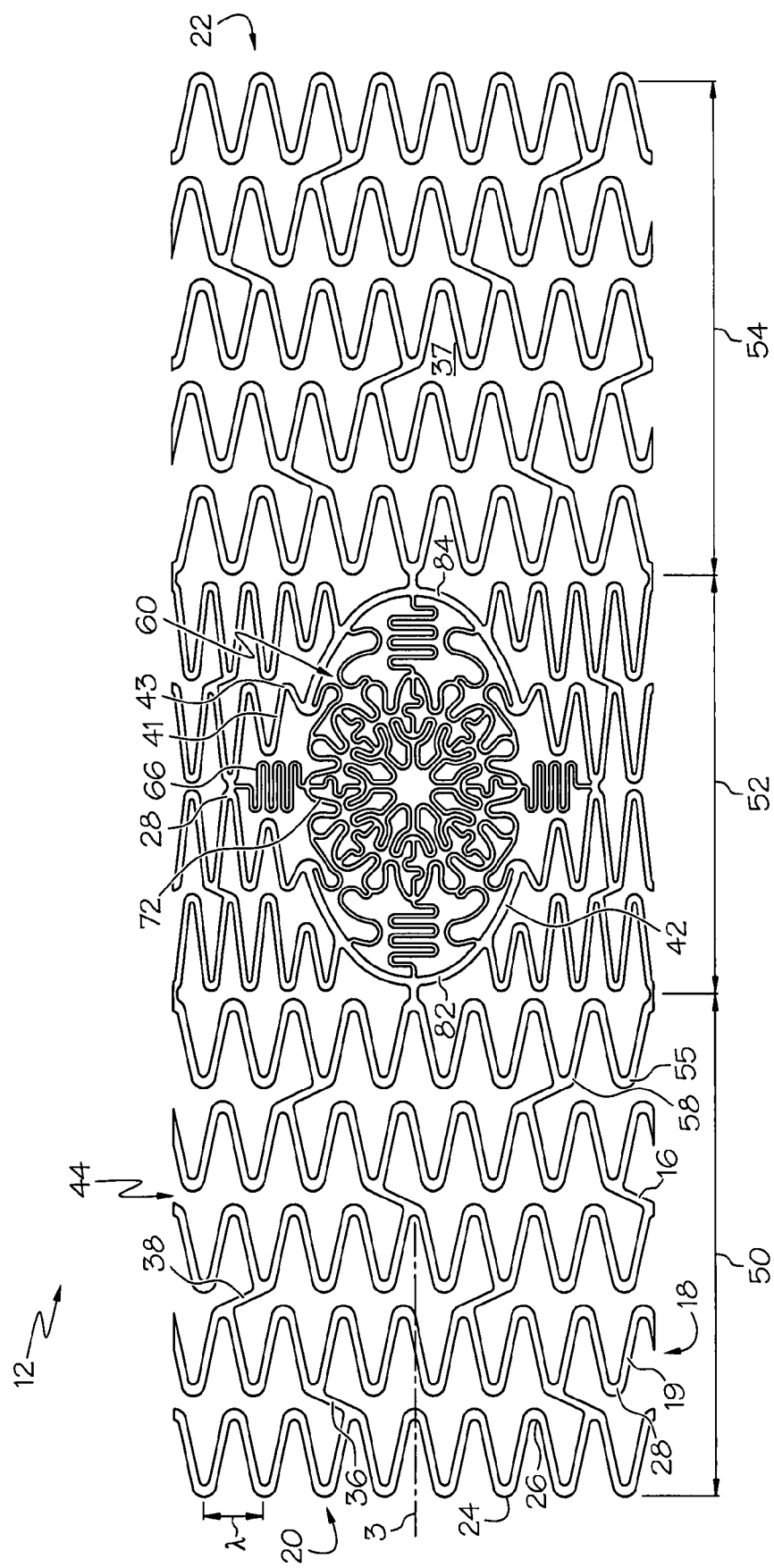
FIG. 15 shows a flat pattern for another embodiment of a stent.

FIG. 15 shows a flat pattern for another embodiment of a stent 12.

In some embodiments, an outer connector 66 can connect between the second serpentine ring 72 and one or more serpentine bands 18. In some embodiments, an outer connector can connect to turns 28 of adjacent serpentine bands 18.

Figure 16:
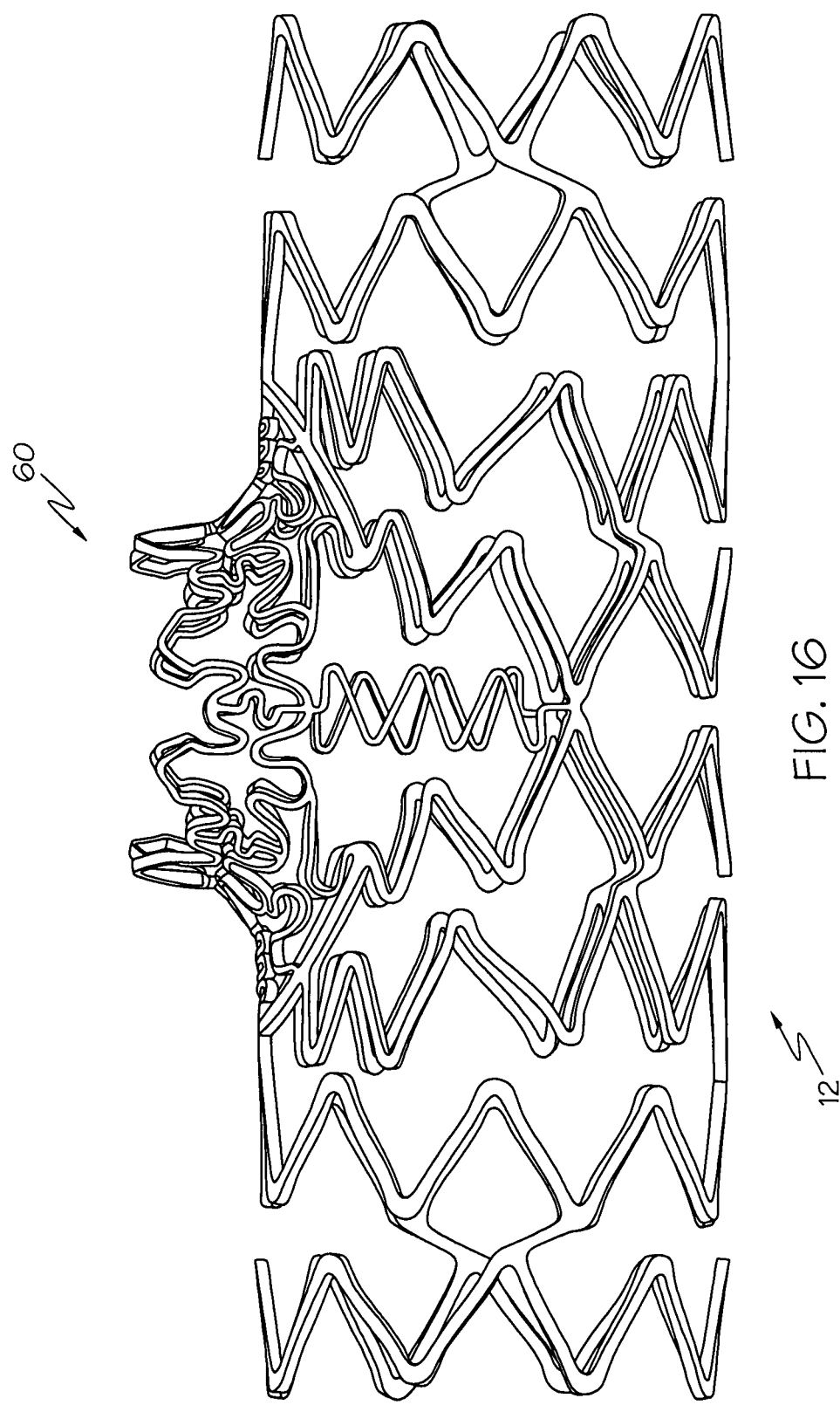
FIG. 16 shows a side view of a stent according to the flat pattern of FIG. 15.

FIG. 16 shows a side view of a stent according to the flat pattern of FIG. 15. The stent 12 is shown in an expanded configuration with the side branch structure 60 outwardly deployed.

Figure 17:
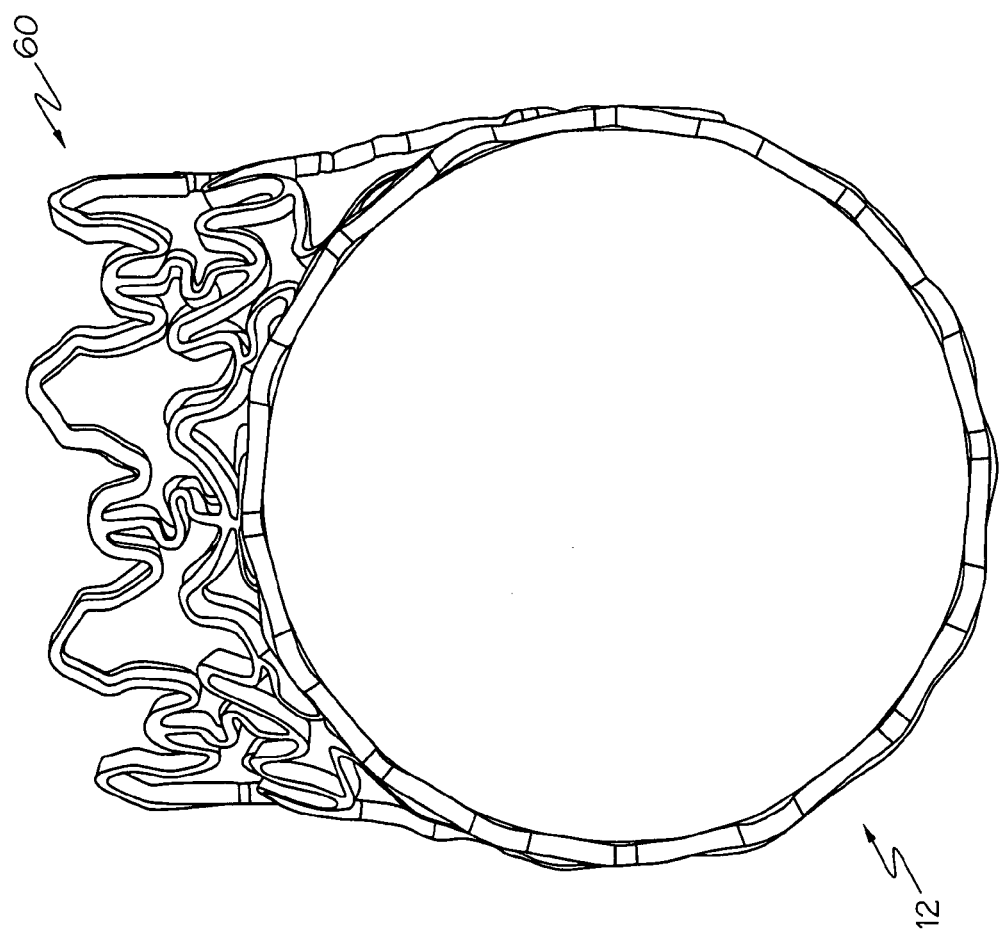
FIG. 17 shows an end view of a stent according to the flat pattern of FIG. 15.

FIG. 17 shows an end view of a stent according to the flat pattern of FIG. 15 in an expanded configuration with the side branch structure 60 outwardly deployed.

Figure 18:
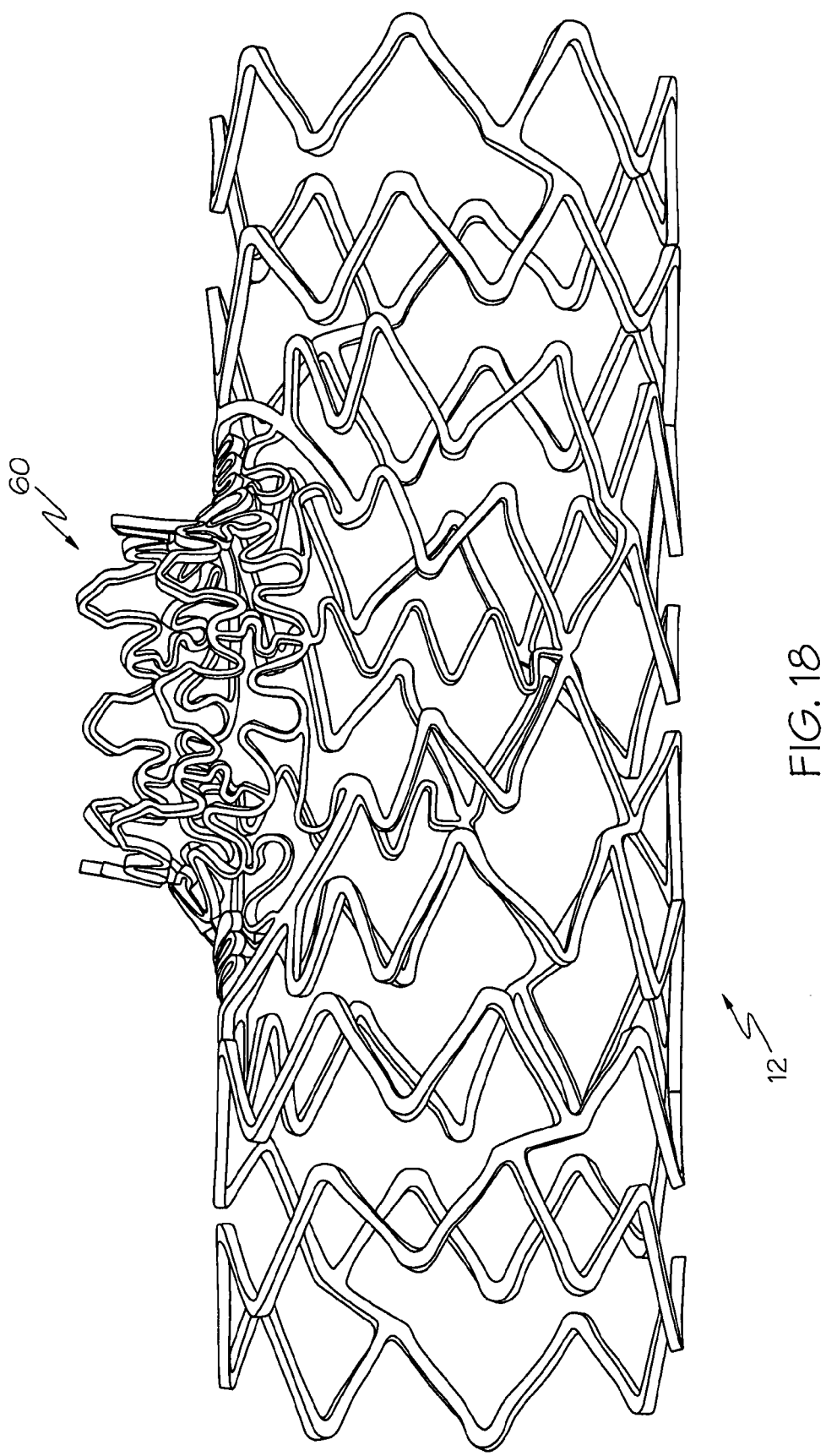
FIG. 18 shows another view of a stent according to the flat pattern of FIG. 15.

FIG. 18 shows a three-dimensional view of a stent according to the flat pattern of FIG. 15 in an expanded configuration with the side branch structure 60 outwardly deployed.

Figure 19:
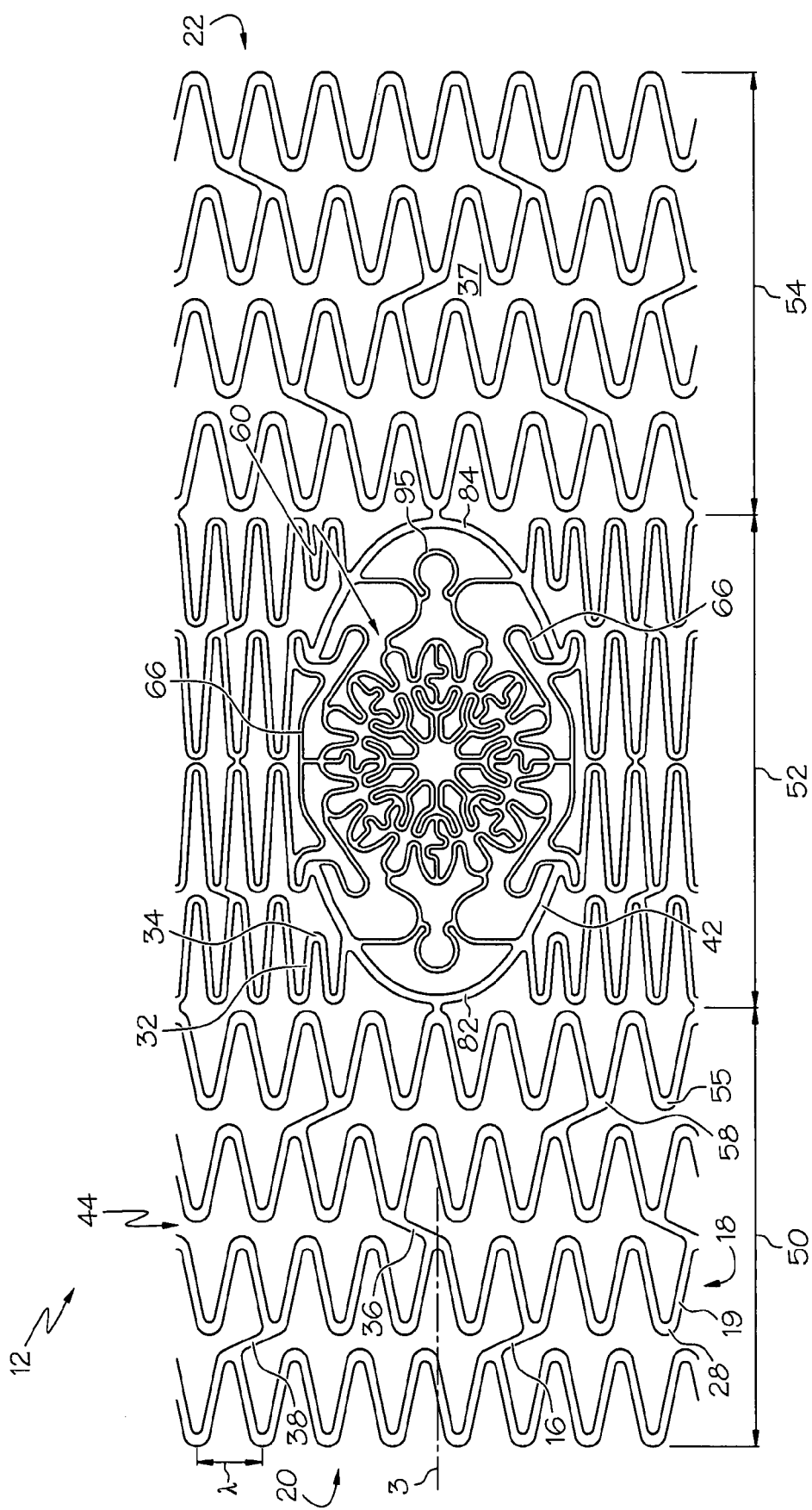
FIG. 19 shows a flat pattern for another embodiment of a stent.
Figure 20:
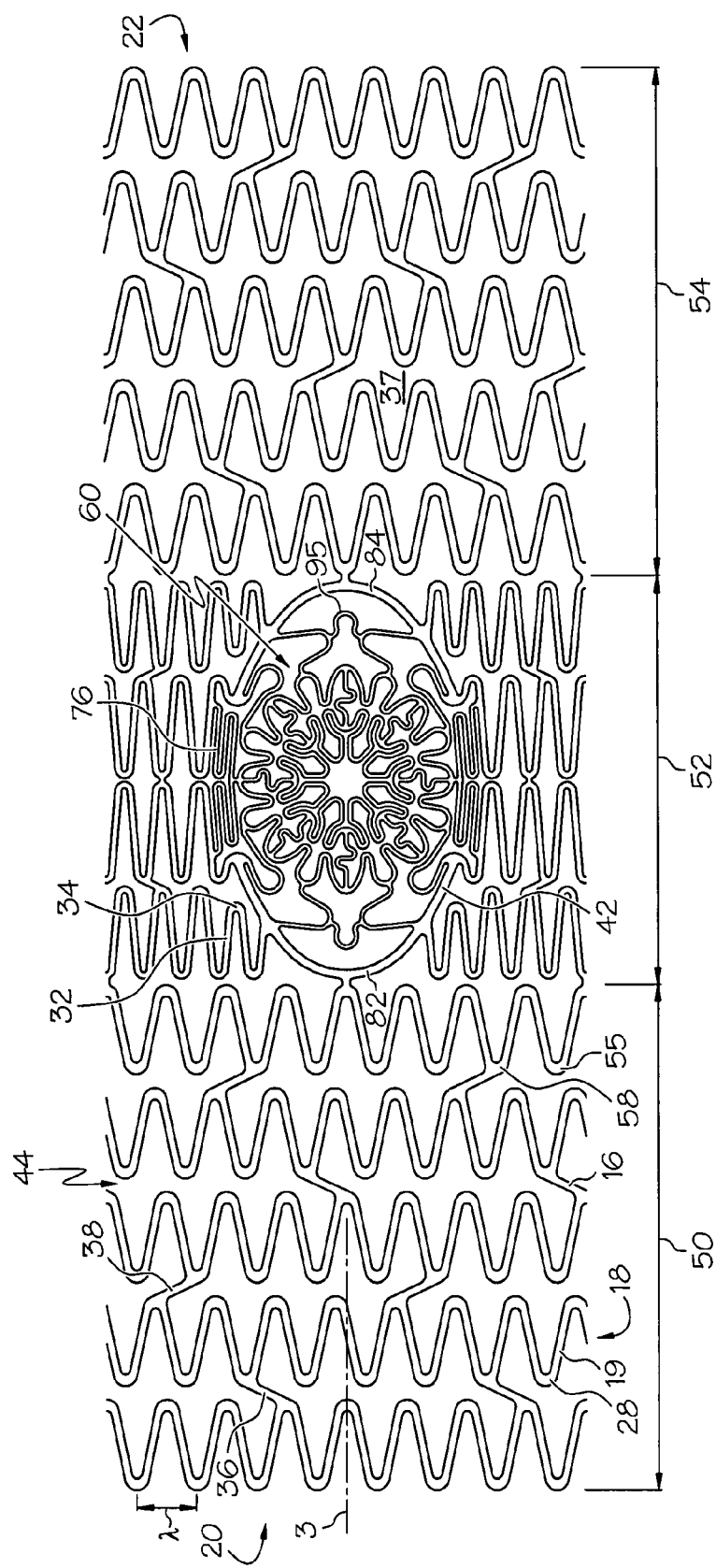
FIG. 20 shows a flat pattern for another embodiment of a stent.
Figure 21:
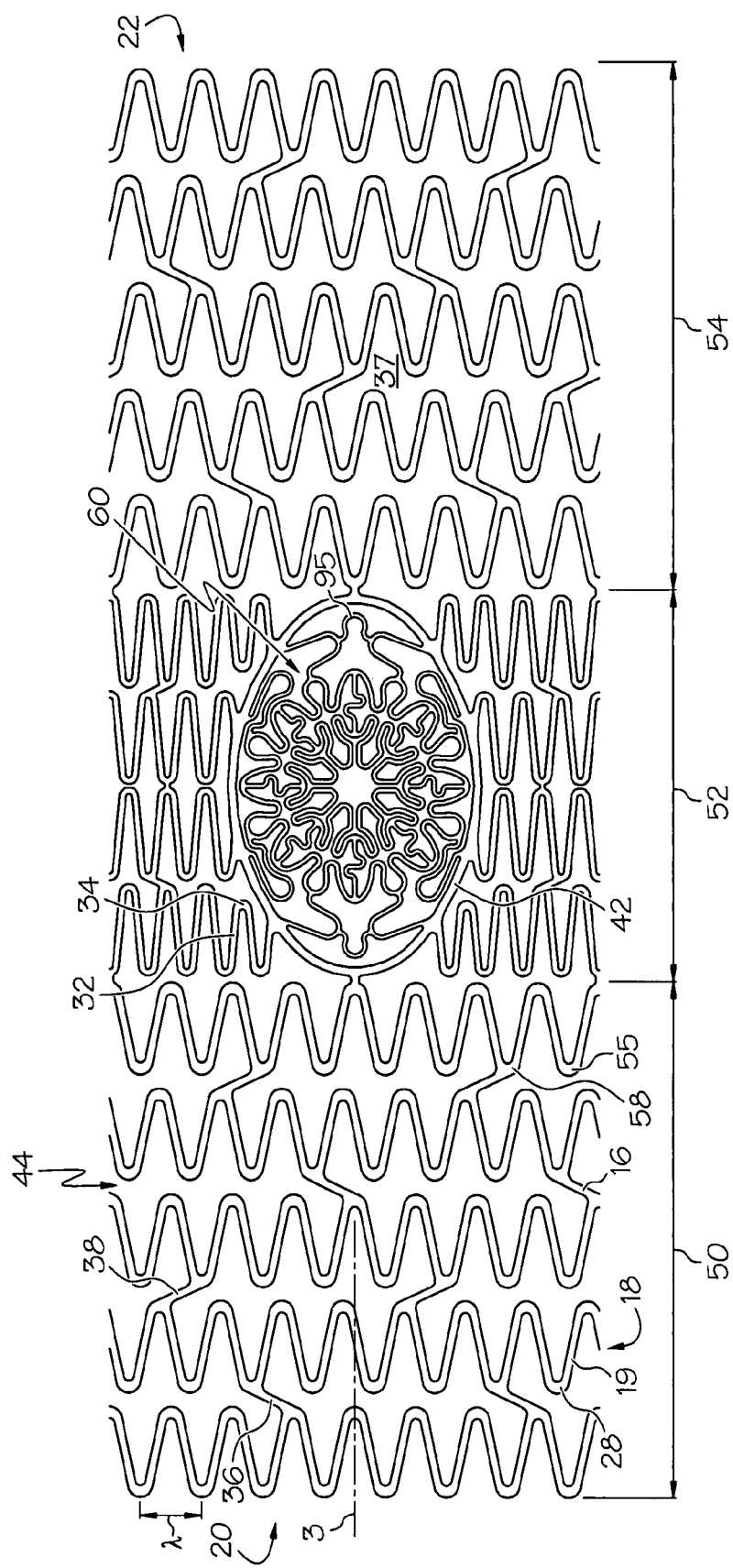
FIG. 21 shows a flat pattern for another embodiment of a stent.

FIGS. 19-21 each show a flat pattern for another embodiment of a stent 12. These Figures show further embodiments of outer side branch connectors 66. In some embodiments, a connecting strut 95 can span between two outer connectors 66.

FIG. 21 further shows another embodiment of a support ring 42.

In some embodiments, the support ring 42 extends continuously around the side branch structure 60. In some embodiments, the support ring 42 comprises a structure that is continuously concave with respect to the side branch center point 68. Thus, in some embodiments, the support ring 42 does not include any portions of curvature that are convex with respect to the side branch center point 68.

Figure 22:
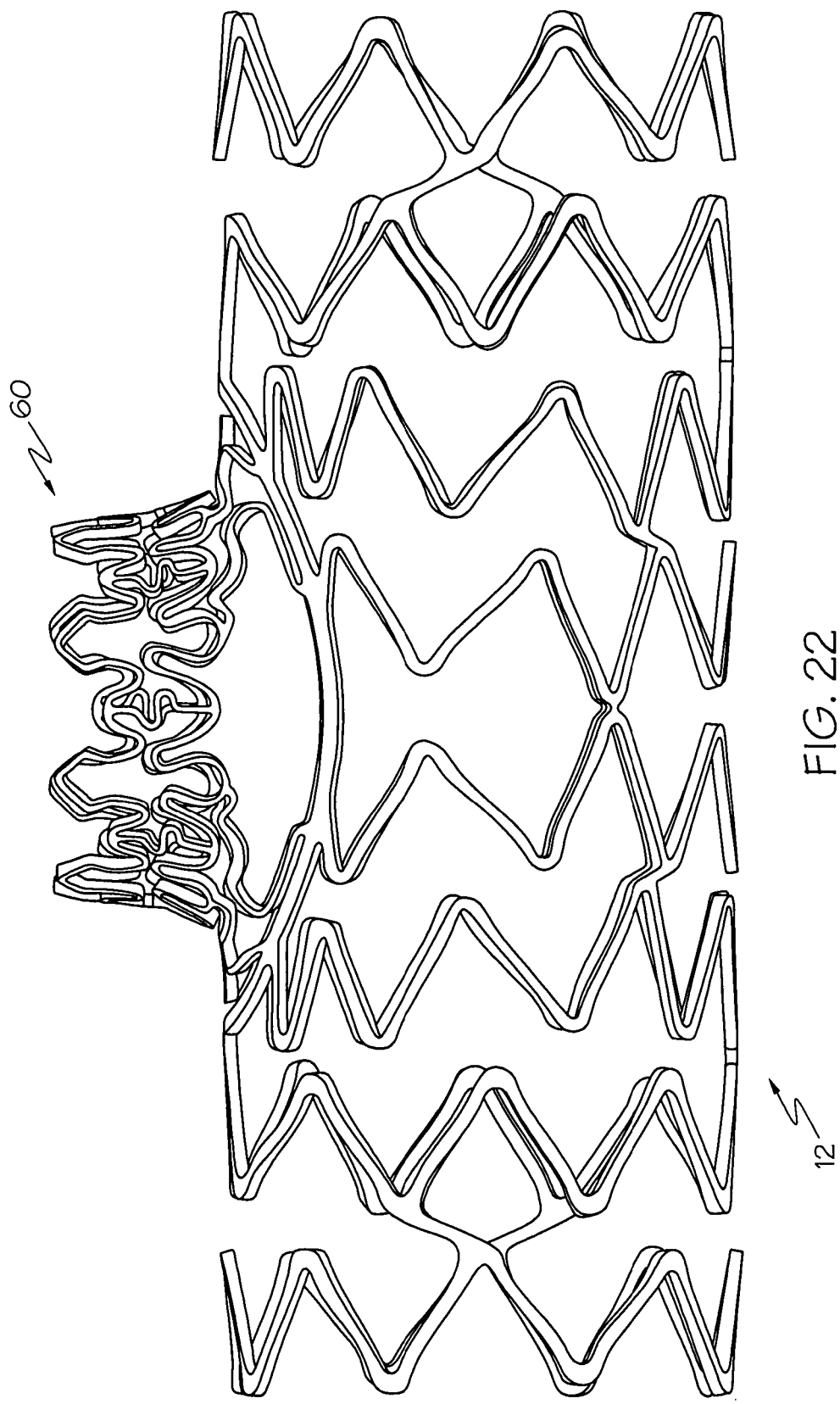
FIG. 22 shows a side view of a stent according to the flat pattern of FIG. 21.

FIG. 22 shows a side view of a stent according to the flat pattern of FIG. 21. The stent 12 is shown in an expanded configuration with the side branch structure 60 outwardly deployed.

Figure 23:
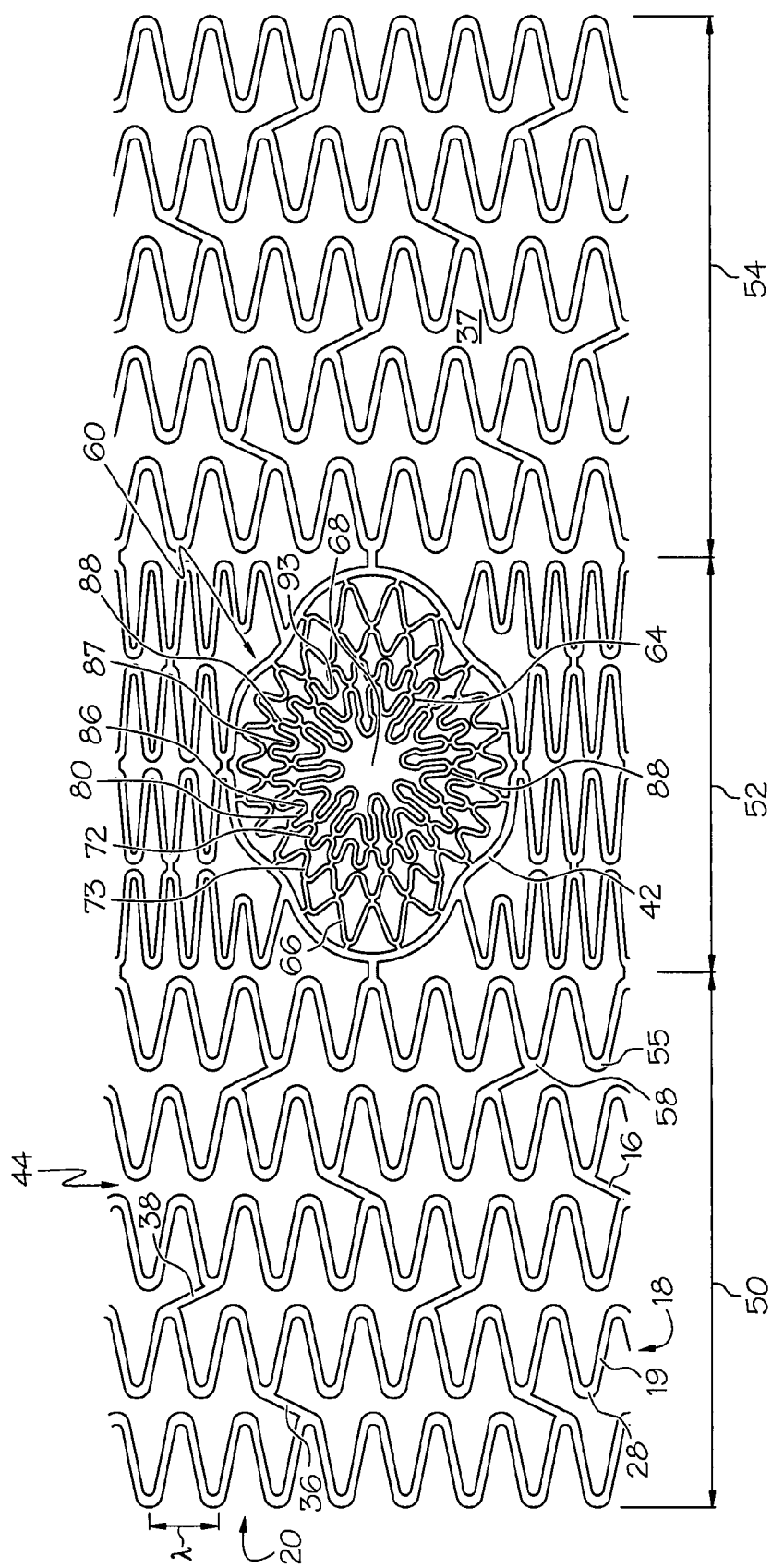
FIG. 23 shows a flat pattern for another embodiment of a stent.

FIG. 23 shows a flat pattern for another embodiment of a stent 12. FIGS. 3 and 5 also show flat patterns for stents having a side branch structure 60 similar to that of FIG. 23.

In some embodiments, the second serpentine ring 72 comprises a plurality of alternating struts 80 and curved portions 86. In some embodiments, each strut 80 is straight along its length. In some embodiments, the curved portions 86 comprise alternating convex portions 87 and concave portions 88.

In some embodiments, an inner connector 64 is straight along its length and is oriented in a side branch radial direction. In some embodiments, an inner connector 64 connects between a concave curved portion 88 of the first serpentine ring 70 and a convex curved portion 87 of the second serpentine ring 72.

In some embodiments, the side branch structure further comprises a third serpentine ring 73 that extends around the second serpentine ring 72. In some embodiments, the third serpentine ring 73 comprises a plurality of alternating struts 80 and curved portions 86. In some embodiments, each strut 80 is straight along its length. In some embodiments, the curved portions 86 comprise alternating convex portions 87 and concave portions 88.

In some embodiments, the third serpentine ring 73 comprises the same number of struts 80 and curved portions 86 as the second serpentine ring 72. In some embodiments, convex portions 87 of the second serpentine ring 72 are radially aligned with concave portions 88 of the third serpentine ring 73, and concave portions 88 of the second serpentine ring 72 are radially aligned with convex portions 87 of the third serpentine ring 73.

In some embodiments, each concave portion 88 of the first serpentine ring 70 connects to a convex portion 87 of the second serpentine ring 72 via a connecting segment or inner connector 64. In some embodiments, the second serpentine ring 72 comprises unconnected convex portions 93 that do not connect to an inner connector 64. In some embodiments, the unconnected convex portions 93 of the second serpentine ring 72 are located closer to the side branch center point 68 than the convex portions 87 that connect to an inner connector 64.

In some embodiments, outer side branch connectors 66 connect between the third serpentine ring 73 and the support ring 42.

Figure 24:
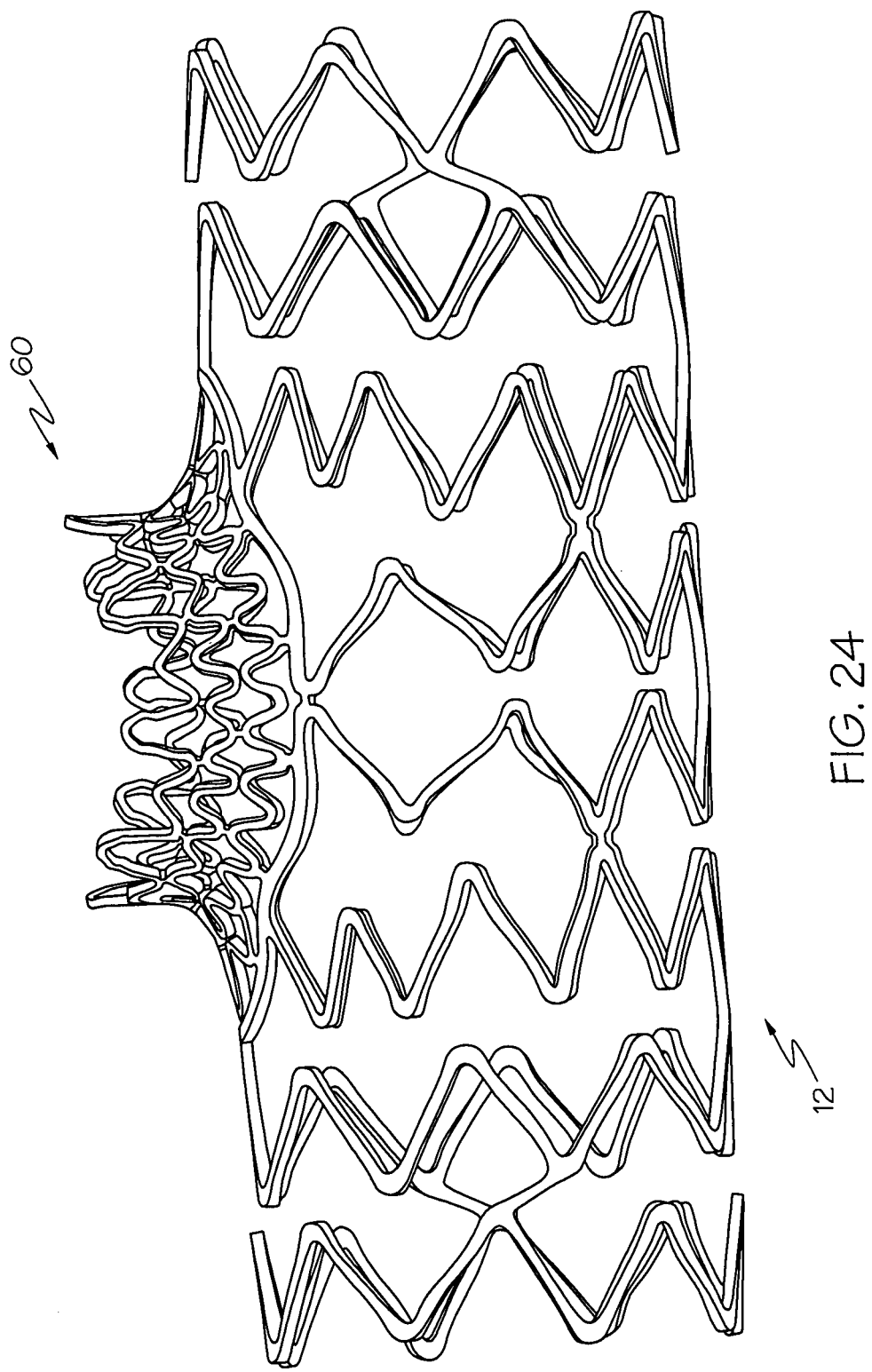
FIG. 24 shows a side view of a stent according to the flat pattern of FIG. 23.

FIG. 24 shows a side view of a stent according to the flat pattern of FIG. 23. The stent 12 is shown in an expanded configuration with the side branch structure 60 outwardly deployed.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The present invention also provides kits comprising a stent or stents according to the present invention. In addition to a stent or stents, a kit according to the present invention may include, for example, delivery catheter(s), balloon(s), and/or instructions for use. In kits according to the present invention, the stent(s) may be mounted in or on a balloon or catheter. Alternatively, the stent(s) may be separate from the balloon or catheter and may be mounted therein or thereon prior to use.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

What is claimed is:

1. A stent comprising:
   a plurality of interconnected framework members defining a plurality of cells, a portion of the interconnected framework members comprising a side branch structure defining an inner side branch cell having a side branch center point, the inner side branch cell being shaped differently than other cells of the stent;
   the side branch structure comprising:
   a first serpentine ring extending around the inner side branch cell, the first serpentine ring comprising a plurality of curved portions including convex curved portions that are convex with respect to the side branch center point, and concave curved portions that are concave with respect to the side branch center point, the convex curved portions including first convex curved portions and second convex curved portions, the second convex curved portions located farther away from a side branch center point than the first convex curved portions;
   a second serpentine ring extending around the first serpentine ring; and
   a plurality of side branch connectors, each side branch connector extending between a second convex curved portion of the first serpentine ring and the second serpentine ring.

2. The stent of claim 1, wherein the second serpentine ring comprises a plurality of alternating straight struts and curved portions.

3. The stent of claim 2, wherein the curved portions of the second serpentine ring comprise alternating convex curved portions and concave curved portions.

4. The stent of claim 3, wherein each side branch connector extends between a convex curved portion of the first serpentine ring and a concave curved portion of the second serpentine ring.

5. The stent of claim 2, the side branch structure further comprising a third serpentine ring extending around the second serpentine ring, third serpentine ring comprising a plurality of alternating straight struts and curved portions.

6. The stent of claim 5, wherein the second serpentine ring and the third serpentine ring comprise the same number of straight struts and curved portions.

7. A stent comprising:
   a plurality of interconnected framework members defining a plurality of cells, a portion of the interconnected framework members comprising a side branch structure defining an inner side branch cell having a side branch center point, the inner side branch cell being shaped differently than other cells of the stent;
   the side branch structure comprising:
   a first serpentine ring extending around the inner side branch cell, the first serpentine ring comprising a plurality of curved portions including convex curved portions that are convex with respect to the side branch center point, and concave curved portions that are concave with respect to the side branch center point, the convex curved portions including first convex curved portions and second convex curved portions, the second convex curved portions located farther away from the side branch center point than the first convex curved portions;
   a second serpentine ring extending around the first serpentine ring; and
   a plurality of side branch connectors extending between the first serpentine ring and the second serpentine ring, at least one side branch connector connected to a second convex curved portion.

8. The stent of claim 7, wherein each second convex curved portion has the same radius of curvature.

9. The stent of claim 8, wherein each second convex curved portion comprises a radius of curvature larger than the radius of curvature of any first convex curved portion.

10. The stent of claim 7, wherein each first convex curved portion has the same radius of curvature.

11. The stent of claim 7, wherein the first convex curved portions are distributed around reference first circle centered upon the side branch center point.

12. The stent of claim 11, wherein the second convex curved portions are distributed around second reference circle centered upon the side branch center point, the second reference circle having a greater diameter than the first reference circle.

13. The stent of claim 7, wherein each curved portion has a constant radius of curvature.

14. The stent of claim 7, wherein each second convex curved portion is connected at one end to a concave curved portion and connected at the other end to another concave curved portion.

15. The stent of claim 14, wherein each concave curved portion has the same radius of curvature.

16. The stent of claim 14, wherein the concave curved portions are distributed around a reference circle centered upon the side branch center point.

17. The stent of claim 7, wherein the second serpentine ring comprises a plurality of curved portions including convex curved portions that are convex with respect to the side branch center point, and concave curved portions that are concave with respect to the side branch center point.

18. The stent of claim 17, wherein each side branch connector extends between a second convex curved portion of the first serpentine ring and a concave portion of the second serpentine ring.

19. The stent of claim 18, wherein at least one side branch connector comprises an s-shape.

20. The stent of claim 7, wherein at least one side branch connector bisects a second convex curved portion.

* * * * *